United States Patent
Imada et al.

(10) Patent No.: US 10,047,186 B2
(45) Date of Patent: Aug. 14, 2018

(54) NOVOLAC PHENOL RESIN, MANUFACTURING METHOD THEREFOR, PHOTOSENSITIVE COMPOSITION, RESIST MATERIAL AND COATING FILM

(71) Applicant: DIC Corporation, Tokyo (JP)

(72) Inventors: Tomoyuki Imada, Chiba (JP); Yusuke Sato, Chiba (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/529,475

(22) PCT Filed: Oct. 8, 2015

(86) PCT No.: PCT/JP2015/078595
§ 371 (c)(1),
(2) Date: May 24, 2017

(87) PCT Pub. No.: WO2016/084495
PCT Pub. Date: Jun. 2, 2016

(65) Prior Publication Data
US 2017/0260315 A1 Sep. 14, 2017

(30) Foreign Application Priority Data

Nov. 25, 2014 (JP) ................................. 2014-237712

(51) Int. Cl.
| | | |
|---|---|---|
| C08G 8/20 | (2006.01) |
| C09D 161/12 | (2006.01) |
| G03F 7/023 | (2006.01) |
| C08L 61/12 | (2006.01) |
| G03F 7/039 | (2006.01) |
| C07C 39/15 | (2006.01) |

(52) U.S. Cl.
CPC ............... *C08G 8/20* (2013.01); *C07C 39/15* (2013.01); *C08L 61/12* (2013.01); *G03F 7/0236* (2013.01); *G03F 7/039* (2013.01); *C08L 2205/025* (2013.01)

(58) Field of Classification Search
CPC .......... C08G 8/20; C08L 61/12; G03F 7/0236
See application file for complete search history.

(56) References Cited

U.S. PATENT DOCUMENTS

| | | | | | |
|---|---|---|---|---|---|
| 5,468,590 A | * | 11/1995 | Hashimoto | ............... | C08G 8/24 430/165 |
| 5,709,977 A | * | 1/1998 | Tan | ....................... | G03F 7/0236 430/191 |
| 5,789,522 A | * | 8/1998 | Zampini | ................... | C08G 8/04 427/352 |
| 5,861,229 A | * | 1/1999 | Osaki | ..................... | G03F 7/0226 430/165 |
| 2008/0182204 A1 | * | 7/2008 | Calvert | ................. | G03F 7/0236 430/281.1 |
| 2010/0203444 A1 | * | 8/2010 | Sung | ...................... | G03F 7/0236 430/270.1 |
| 2013/0244174 A1 | | 9/2013 | Imada et al. | | |
| 2014/0023969 A1 | | 1/2014 | Imada et al. | | |
| 2014/0363915 A1 | * | 12/2014 | Tsai | ....................... | G03F 7/0382 438/46 |
| 2017/0121444 A1 | * | 5/2017 | Imada | ...................... | C08G 8/08 |
| 2017/0329221 A1 | * | 11/2017 | Imada | ................... | G03F 7/0236 |

FOREIGN PATENT DOCUMENTS

| | | |
|---|---|---|
| JP | 02-055359 A | 2/1990 |
| JP | 09-090626 A | 4/1997 |
| JP | 5035492 B2 | 9/2012 |
| JP | 5152447 B2 | 2/2013 |

OTHER PUBLICATIONS

International Search Report dated Dec. 8, 2015 issued in International Patent Application No. PCT/JP2015/078595 (with English translation).

* cited by examiner

*Primary Examiner* — Cynthia Hamilton
(74) *Attorney, Agent, or Firm* — McDermott Will & Emery LLP

(57) ABSTRACT

The present invention provides a photosensitive composition having excellent heat resistance, low absorbance at the exposure light at wavelengths of g-line, h-line, and i-line, and satisfactory sensitivity even when the thickness of a resist film is increased, and also provides a resist material, a coating film thereof, a novolac phenol resin suitable for these applications, and a method for producing the phenol resin. Specifically, there is provided a novolac phenol resin produced by reacting a phenolic trinuclear compound (A) with formaldehyde under an acid catalyst, the phenolic trinuclear compound (A) including a phenolic trinuclear compound (A1) produced by condensation reaction of dialkyl-substituted phenol with a hydroxyl group-containing aromatic aldehyde and a phenol trinuclear compound (A2) produced by condensation reaction of dialkyl-substituted phenol having alkyl groups at the 2- and 3-positions, 2- and 5-position, the 3- and 4-positions, or 3- and 5-positions with an aromatic aldehyde not having a hydroxyl group, wherein the molar ratio of the phenolic trinuclear compound (A1) to the phenolic trinuclear compound (A2) is 20:80 to 90:10.

9 Claims, 5 Drawing Sheets

[minutes]

[minutes]

NOVOLAC PHENOL RESIN, MANUFACTURING METHOD THEREFOR, PHOTOSENSITIVE COMPOSITION, RESIST MATERIAL AND COATING FILM

CROSS REFERENCE

This patent application is the U.S. National Phase under 35 U.S.C. § 371 of International Application No. PCT/JP2015/078595, filed on Oct. 8, 2015, which claims the benefit of Japanese Patent Application No. 2014-237712, filed on Nov. 25, 2014.

TECHNICAL FIELD

The present invention relates to a photosensitive composition having excellent heat resistance, low absorbance at the exposure light wavelengths of g-line, h-line, and i-line, and satisfactory sensitivity even when the thickness of a resist coating film is increased, and also relates to a resist material, a coating film thereof, and a novolac phenol resin suitable for these applications.

BACKGROUND ART

Positive photoresists using an alkali-soluble resin and a photosensitizer such as a 1,2-naphthoquinone diazide compound or the like are known as resists used for manufacturing semiconductors such as IC, LSI, and the like and manufacturing display devices such as LCD and the like, and manufacturing printing original plates. There is proposed a positive photoresist composition using, as the alkali-soluble resin, a mixture containing a m-cresol novolac resin and p-cresol novolac resin as the alkali-soluble resin (for example, refer to Patent Literature 1).

The positive photoresist composition described in Patent Literature 1 is developed for the purpose of improving developability such as sensitivity and the like. However, recent increasing integration of semiconductors has brought about a tendency toward finer pattern lines and a demand for more excellent sensitivity, and the positive photoresist composition described in Patent Literature 1 has the problem that satisfactory sensitivity coping with finer lines cannot be achieved. Further, various heat treatments are performed in a process for manufacturing a semiconductor or the like, and thus a coating film of the positive photoresist composition is required to have high heat resistance. However, the positive photoresist composition described in Patent Literature 1 has the problem of unsatisfactory heat resistance.

Also, there is proposed, as a phenol resin having excellent resistivity and high heat resistance, a phenol resin for photoresist which is produced by reacting phenol such as m-cresol, p-cresol, or 2,3-xylenol with an aromatic aldehyde and then adding aldehyde (B) to the resultant reaction product and reacting both under an acid catalyst (for example, refer to Patent Literature 2). The phenol resin for photoresist has improved sensitivity as compared with usual ones but cannot satisfactorily cope with a recent high requirement level of heat resistance.

On the other hand, the photosensitivity of a novolac resin which is an alkali-soluble resin can be enhanced by improving alkali solubility. However, improvement in alkali solubility tends to decrease heat resistance, and improvement in heat resistance has the problem of decreasing photosensitivity. Therefore, it is difficult to satisfy high levels of both sensitivity and heat resistance of a novolac resin. There is proposed, as a resin increased in both sensitivity and heat resistance, a novolac phenol resin for photoresist using as a raw material a phenolic trinuclear compound produced by condensation of xylenol with a phenolic hydroxyl group-containing aromatic aldehyde (for example, refer to Patent Literatures 3 and 4).

CITATION LIST

Patent Literature

PTL 1: Japanese Unexamined Patent Application Publication No. 2-55359
PTL 2: Japanese Unexamined Patent Application Publication No. 9-90626
PTL 3: Japanese Patent No. 5152447
PTL 4: Japanese Patent No. 5035492

SUMMARY OF INVENTION

Technical Problem

The novolac phenol resin described in Patent Literature 3 or 4 has high levels of both sensitivity and heat resistance as compared with usual ones, but has absorption at i-line (365 nm) used for exposure in photolithography. Therefore, the novolac phenol resin has the problem of decreasing sensitivity when the thickness of a resist coating film is increased.

Accordingly, a problem to be solved by the present invention is to provide a photosensitive composition having excellent heat resistance, low absorbance at the exposure wavelengths of g-line, h-line, and i-line, and satisfactory sensitivity even when the thickness of a resist film is increased, and also provides to a resist material, a coating film thereof, a novolac phenol resin suitable for these applications, and a method for producing the phenol resin.

Solution to Problem

As a result of repeated earnest investigations for solving the problem, the inventors found that a novolac phenol resin produced by condensation of a phenolic trinuclear compound with aldehyde (B) has low absorbance at the exposure wavelengths of g-line, h-line, and i-line while maintaining high heat resistance and thus can be used for a resist material capable of forming a pattern with high sensitivity even when the thickness of a resist coating film is increased, the phenolic trinuclear compound including a combination at a specific molar ratio of a phenolic trinuclear compound, which is produced by condensation reaction of dialkyl-substituted phenol with a hydroxyl group-containing aromatic aldehyde, to a phenolic trinuclear compound, which is produced by condensation reaction of dialkyl-substituted phenol having alkyl groups at the 2- and 3-positions, the 2- and 5-position, the 3- and 4-positions, or the 3- and 5-positions with an aromatic aldehyde not having a hydroxyl group. This finding led to the achievement of the present invention.

That is, the present invention relates to a novolac phenol resin produced by reacting a phenolic trinuclear compound (A) with aldehyde (B) under an acid catalyst, the phenolic trinuclear compound (A) including a phenolic trinuclear compound (A1) produced by condensation reaction of dialkyl-substituted phenol with a hydroxyl group-containing aromatic aldehyde and a phenolic trinuclear compound (A2) produced by condensation reaction of dialkyl-substituted phenol having alkyl groups at the 2- and 3-positions, the 2- and 5-position, the 3- and 4-positions, or the 3- and 5-positions with an aromatic aldehyde not having a hydroxyl group, and the molar ratio of the phenolic trinuclear compound (A1) to the phenolic trinuclear compound (A2) being 20:80 to 90:10.

The present invention also relates to a method for producing the novolac phenol resin.

The present invention further relates to a photosensitive composition containing the novolac phenol resin, a resist material including the photosensitive composition, and a coating film including the resist material.

Advantageous Effects of Invention

A novolac phenol resin, a photosensitive composition containing the novolac phenol resin, and a resist material including the photosensitive composition have high heat resistance and sensitivity and low absorbance at the exposure light wavelengths of g-line, h-line, and i-line. Therefore, the use of the resist material can provide a resist coating film capable of forming a pattern with high sensitivity even when the film has a large thickness.

DESCRIPTION OF EMBODIMENTS

Figure 1:
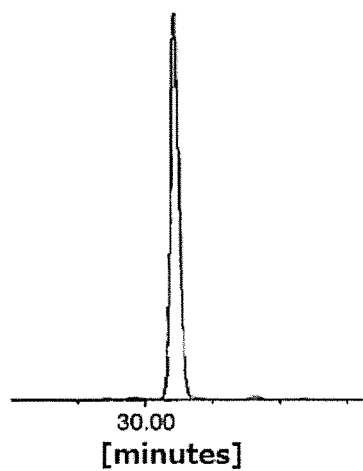
FIG. 1 is a GPC chart of a phenolic trinuclear compound (1) produced in Synthesis Example 1.

A novolac phenol resin according to the present invention is produced by reacting a phenolic trinuclear compound (A) with aldehyde (B) under an acid catalyst, the phenolic trinuclear compound (A) including a phenolic trinuclear compound (A1) produced by condensation reaction of dialkyl-substituted phenol with a hydroxyl group-containing aromatic aldehyde and a phenolic trinuclear compound (A2) produced by condensation reaction of dialkyl-substituted phenol having alkyl groups at the 2- and 3-positions, the 2- and 5-position, the 3- and 4-positions, or the 3- and 5-positions with an aromatic aldehyde not having a hydroxyl group, and the molar ratio of the phenolic trinuclear compound (A1) to the phenolic trinuclear compound (A2) being 20:80 to 90:10.

The phenolic trinuclear compound (A1) has absorption at i-line (365 nm), while the phenolic trinuclear compound (A2) which is a trinuclear compound composed of two benzene rings each having a phenolic hydroxyl group and a benzene ring not having a phenolic hydroxyl group has no absorption at the exposure wavelengths of g-line, h-line, and i-line. Therefore, the absorbance of the resultant novolac phenolic resin at the exposure wavelengths of g-line, h-line, and i-line can be suppressed by using not only the phenolic trinuclear compound (A1) but also the phenolic trinuclear compound (A2) as the phenolic trinuclear compound (A) to be condensed with the aldehyde (B). Also, the sensitivity of the resultant novolac phenolic resin can be improved without decreasing heat resistance by using, as the phenolic trinuclear compound (A2) used as a raw material, a phenolic trinuclear compound produced by condensation reaction with an aromatic aldehyde having alkyl groups at the 2- and 3-positions, the 2- and 5-position, the 3- and 4-positions, or the 3- and 5-positions as compared with a phenolic trinuclear compound produced by using only the phenolic trinuclear compound (A1).

The phenolic trinuclear compound (A1) used in the present invention is produced by condensation reaction of dialkyl-substituted phenol with a hydroxyl group-containing aromatic aldehyde. The condensation reaction is performed under conditions which can employ a difference in reaction activation energy between carbon atoms on an aromatic hydrocarbon group of the dialkyl-substituted phenol (c1). Specifically, for example, the phenolic trinuclear compound (A1) can be produced by polycondensation of the dialkyl-substituted phenol (c1) with a hydroxyl group-containing aromatic aldehyde (c2) in the presence of an acid catalyst.

The dialkyl-substituted phenol (c1) is a compound in which the two hydrogen atoms bonded to a benzene ring of phenol are substituted by alkyl groups. By using the dialkyl-substituted phenol as a raw material, the phenolic trinuclear compound (A1) becomes a phenolic trinuclear compound which can produce a novolac phenol resin having a god balance between heat resistance and alkali solubility. The alkyl group is, for example, an alkyl group having 1 to 8 carbon atoms, which may have a substituent. Examples of the dialkyl-substituted phenol (c1) include 2,5-xylenol, 3,5-xylenol, 3,4-xylenol, 2,3-xylenol, 2,4-xylenol, 2,6-xylenol, and the like. These dialkyl-substituted phenols (c1) can be used alone or in combination of two or more, but are preferably used alone. In particular, 2,5-xylenol is preferred because it produces a phenolic trinuclear compound which can produce a novolac phenol resin having an excellent balance between heat resistance and alkali solubility.

The hydroxyl group-containing aromatic aldehyde (c2) is a compound having at least one aldehyde group and at least one hydroxyl group in the aromatic ring. Examples of the hydroxyl group-containing aromatic aldehyde (c2) include salicylaldehyde, hydroxybenzaldehyde such as m-hydroxybenzaldehyde, p-hydroxybenzaldehyde, and the like, dihydroxybenzaldehyde such as 2,4-dihydroxybenzaldehyde, 3,4-dihydroxybenzaldehyde, and the like, and vanilline-based compounds such as vanilline, orthovanilline, isovanilline, ethylvanilline, and the like. Among these hydroxyl group-containing aromatic aldehydes (c2), p-hydroxybenzaldehyde(4-hydroxybenzaldehde), 2,4-dihydroxybenzaldehyde, and 3,4-dihydroxybenzaldehyde are preferred, and p-hydroxybenzaldehyde is more preferred because of easy industrial availability and an excellent balance between heat resistance and alkali solubility. These hydroxyl group-containing aromatic aldehydes (c2) can be used alone or in combination of two or more, but are preferably used alone.

Among compounds produced by condensation reaction of the dialkyl-substituted phenol (c1) with the hydroxyl group-containing aromatic aldehyde (c2), the phenolic trinuclear compound (A1) is preferably a compound produced by using 2,5-xylenol as the dialkyl-substituted phenol (c1), more preferable a compound produced by condensation reaction of 2,5-xylenol with p-hydroxybenzaldehyde(4-hydroxybenzaldehyde), 2,4-dihydroxybenzaldehyde, or 3,4- dihydroxybenzaldehyde, and still more preferably a compound produced by condensation reaction of 2,5-xylenol with p-hydroxybenzaldehyde.

Examples of the acid catalyst used in condensation reaction of the dialkyl-substituted phenol (c1) with the hydroxyl group-containing aromatic aldehyde (c2) include acetic acid, oxalic acid, sulfuric acid, hydrochloric acid, phenolsulfonic acid, para-toluenesulfonic acid, zinc acetate, manganese acetate, and the like. These acid catalysts can be used alone or in combination of two or more. Among these acid catalysts, sulfuric acid and para-toluenesulfonic acid are preferred in view of excellent activity. The acid catalyst may be added before the reaction or may be added during the reaction.

If required, polycondensation of the dialkyl-substituted phenol (c1) with the hydroxyl group-containing aromatic aldehyde (c2) may be performed in the presence of an organic solvent. Examples of the organic solvent include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, ethylene glycol monophenyl ether, and the like; cyclic ethers such as 1,3-dioxane, 1,4-dioxane, and the like; glycol esters such as ethylene glycol acetate and the like; and ketones such as acetone, methyl ethyl ketone, methyl isobutyl ketone, and the like. These organic solvents can be used alone or in combination or two or more. Among these organic solvents, 2-ethoxyethaol is preferred in view of excellent solubility of the resultant compound.

The reaction temperature of polycondensation of the dialkyl-substituted phenol (c1) with the hydroxyl group-containing aromatic aldehyde (c2) is, for example, 60° C. to 140° C. Also, the reaction time is, for example, 0.5 to 100 hours.

The charging ratio [(c1)/(c2)] expressed in terms of molar ratio of the dialkyl-substituted phenol (c1) to the hydroxyl group-containing aromatic aldehyde (c2) is preferably within a range of 1/0.2 to 1/0.5 and more preferably within a range of 1/0.25 to 1/0.45 because of excellent removability of the unreacted dialkyl-substituted phenol (c1) and excellent yield of the product and purity of the reaction product.

The reaction solution of polycondensation of the dialkyl-substituted phenol (c1) with the hydroxyl group-containing aromatic aldehyde (c2) may contain an unreacted product remaining together with the phenolic trinuclear compound (A) produced as an intended polycondensate. Also, an undesired polycondensate other than the phenolic trinuclear compound (a1) may be produced. Therefore, the phenolic trinuclear compound (A1) is preferably isolated and purified from the reaction solution (condensate) after the polycondensation reaction before being used as a raw material (the phenolic trinuclear compound (A)) of the novolac phenol resin of the present invention. The purity of the phenolic trinuclear compound (A1) used as the phenolic trinuclear compound (A) is preferably 85% or more, more preferably 90% or more, still more preferably 94% or more, and particularly preferably 98% or more. In the present invention and the description thereof, the purity of the phenolic trinuclear compound can be determined from an area ratio in a GPC chart.

A method for increasing the purity of the phenolic trinuclear compound (A1) by purification is, for example, a method in which the reaction solution after polycondensation reaction is poured into a poor solvent (S1) in which the phenolic trinuclear compound (A1) is insoluble or slightly soluble, filtering off the resultant precipitate, dissolving the precipitate in a solvent (S2) which dissolves the phenolic trinuclear compound (A1) and is miscible with the poor solvent (S1), again pouring the resultant solution in the poor solvent (S1), and then filtering off the produced precipitate. Examples of the poor solvent (S1) used in this method include water; monoalcohols such as methanol, ethanol, propanol, and the like; aliphatic hydrocarbons such as n-hexane, n-heptane, n-octane, cyclohexane, and the like; and aromatic hydrocarbons such as toluene, xylene, and the like. Among these poor solvents (S1), water and methanol are preferred because the acid catalyst can be simultaneously efficiently removed. On the other hand, examples of the solvent (S2) include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, ethylene glycol monophenyl ether, and the like; cyclic ethers such as 1,3-dioxane, 1,4-dioxane, and the like; glycol esters such as ethylene glycol acetate and the like; and ketones such as acetone, methyl ethyl ketone, methyl isobutyl ketone, and the like. When water is used as the poor solvent (S1), acetone is preferred as the solvent (S2). These poor solvents (S1) can be used alone or in combination of two or more, and also the solvents (S2) can be used alone or in combination of two or more.

Examples of the phenolic trinuclear compound (A1) include a compound represented by general formula (1) below. In the general formula (1), r represents an integer of 0 to 4, and s represents 1 or 2. In addition, the sum of r and s is 5 or less.

[Chem. 1]

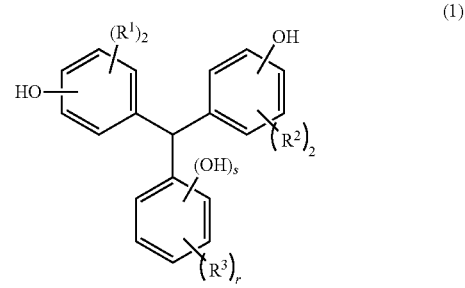

(1)

In the general formula (1), $R^1$, $R^2$, and $R^3$ each independently represent an alkyl group having 1 to 8 carbon atoms, which may have a substituent. The plurality of $R^1$ present may be the same or different, and the plurality of $R^2$ present may be the same or different. When a plurality of $R^3$ are present, they may be the same or different.

An alkyl group of $R^1$, $R^2$, or $R^3$ may be linear or branched or may have a cyclic structure, but is preferably a linear group. In the present invention, an alkyl group of $R^1$, $R^2$, or $R^3$ is preferably an alkyl group having 1 to 6 carbon atoms and more preferably an alkyl group having 1 to 3 carbon atoms.

In the general formula (1), a hydrogen atom in an alkyl group of $R^1$, $R^2$, or $R^3$ may be substituted by a substituent. The number of hydrogen atoms which can be substituted is not particularly limited but is preferably 1 to 3 and more preferably 1 or 2. Also, when an alkyl group of 1 has a plurality of substituents, the substituents may be the same or different.

Examples of the substituent include a hydroxyl group, an alkoxy group having 1 to 6 carbon atoms, an aryl group which may have a substituent, a halogen atom, and the like. Examples of an alkoxy group having 1 to 6 carbon atoms among the substituents possessed by the alkyl group include a methoxy group, an ethoxy group, a propoxy group, a n-butyloxy group, a tert-butyloxy group, a pentyloxy group, an isoamyloxy group, a hexyloxy group, a cyclohexyloxy group, and the like. Examples of an aryl group which may have a substituent include a phenyl group, a naphthyl group, an indenyl group, a biphenyl group, and the like. Examples of a halogen atom include a fluorine atom, a chlorine atom, a bromine atom, and the like.

Examples of an alkyl group of $R^1$, $R^2$, or $R^3$ in the general formula (1) include a methyl group, an ethyl group, a propyl group, an isopropyl group, a n-butyl group, an isobutyl group, a tert-butyl group, a pentyl group, an isoamyl group, a hexyl group, a cyclohexyl group, a hydroxyethyl group, a hydroxypropyl group, a fluoromethyl group, a methoxyethyl group, an ethoxyethyl group, a methoxypropyl group, a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, a dihydroxynaphthylethyl group, and the like. $R^1$ or $R^2$ is preferably a methyl group, an ethyl group, a propyl group, an isopropyl group, a n-butyl group, an isobutyl group, a tert-butyl group, a pentyl group, an isoamyl group, or a hexyl group, more preferably a methyl group or an ethyl group, and still more preferably a methyl group.

In the general formula (1), $R^1$ and $R^2$ are preferably the same group. Also, in a benzene ring to which each of $R^1$ and $R^2$ is bonded, $R^1$ and $R^2$ are preferably bonded to carbon atoms at the same position as viewed from the carbon atoms to which phenolic hydroxyl groups of the benzene rings are respectively bonded. The phenolic hydroxyl group is bonded to each of the benzene rings to which $R^1$ and $R^2$ are respectively bonded, and the bonding positions of the respective phenolic hydroxyl groups are preferably the same position in the benzene rings.

Examples of the compound represented by the general formula (1) include compounds represented by any of general formulae (1-1) to (1-18) below. In the general formulae (1-1) to (1-18), $R^1$, $R^2$, and $R^3$ represent the same meanings as in the general formula (1), r1 represents an integer of 0 to 4, and r2 represents an integer of 0 to 3. The compounds represented by the general formulae (1-1) to (1-18) are preferably compounds in which both $R^1$ and $R^2$ are methyl groups or ethyl groups and r1 and r2 are 0, and more preferably compounds in which both $R^1$ and $R^2$ are methyl groups and r1 and r2 are 0.

[Chem. 2]

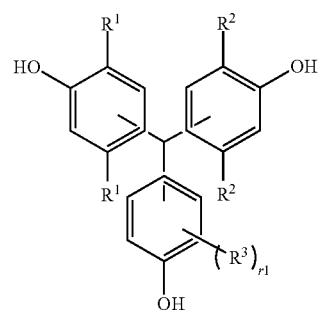
(1-1)

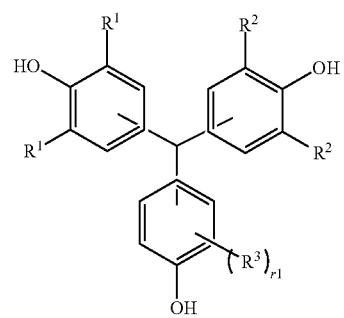
(1-2)

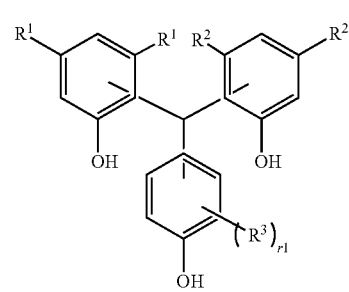
(1-3)

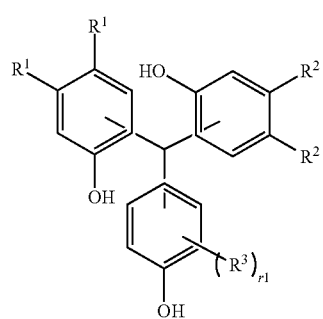
(1-4)

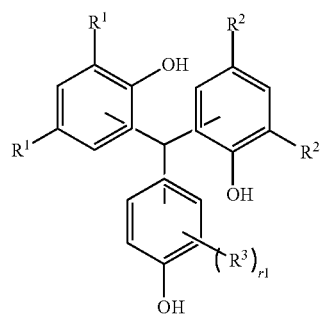
(1-5)

(1-6)
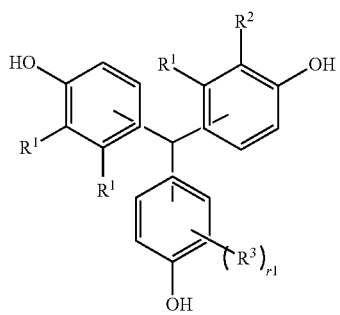
[Chem. 3]
(1-7)
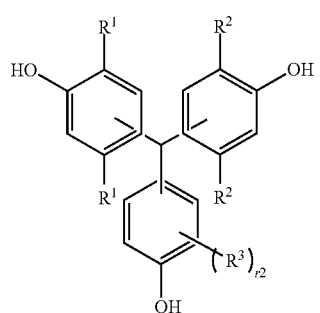
(1-8)
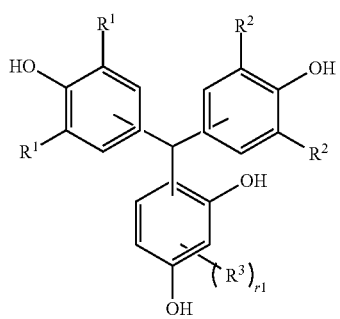
(1-9)
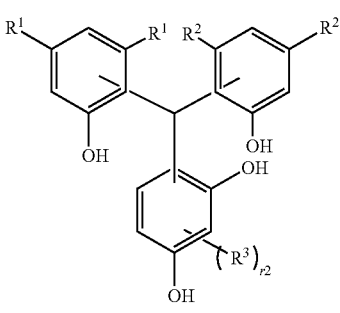
(1-10)
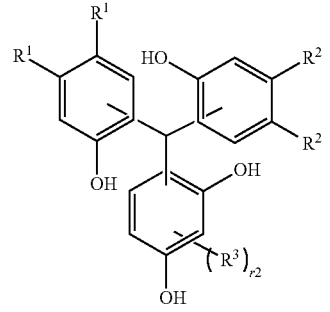
(1-11)
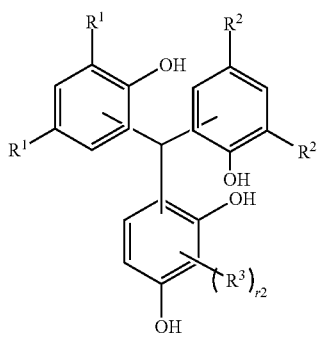
(1-12)
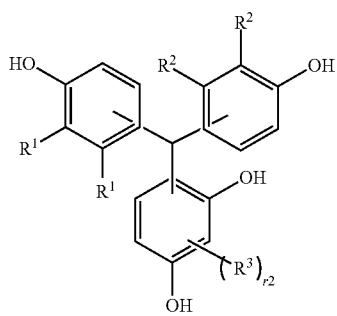
[Chem. 4]
(1-13)
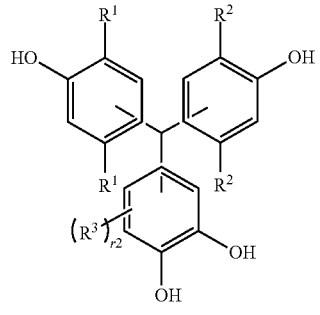
(1-14)
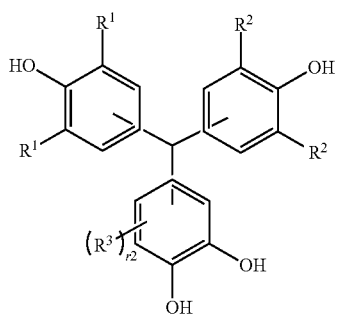
(1-15)
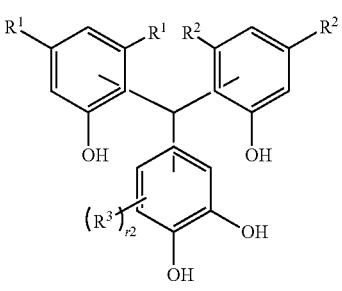

(1-16)
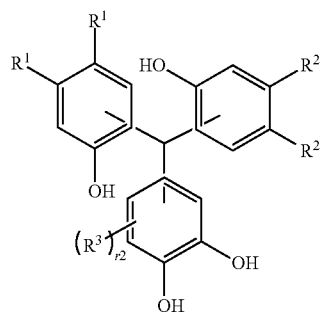

(1-17)
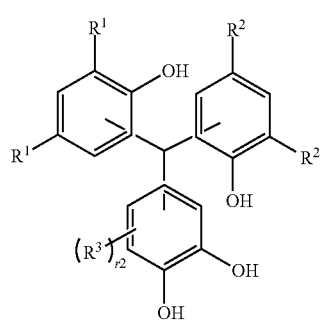

(1-18)
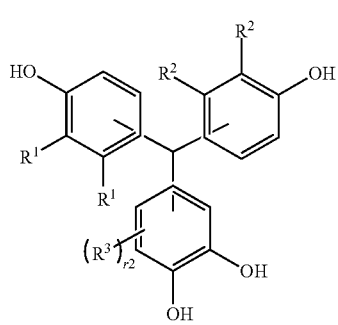

Because the novolac phenol resin which can produce a coating film having heat resistance and high resolution can be produced, the phenolic trinuclear compound (A1) is preferably a compound represented by the general formula (1-1), (1-2), (1-7), (1-8), (1-13), or (1-14), more preferably a compound represented by the general formula (1-1), (1-7), or (1-13), and even more preferably a compound represented by the general formula (1-1).

The phenolic trinuclear compound (A2) used in the present invention can be produced by condensation reaction of the dialkyl-substituted phenol having alkyl groups at the 2- and 3-positions, the 2- and 5-position, the 3- and 4-positions, or the 3- and 5-positions with the aromatic aldehyde (hydroxyl group-non-containing aromatic aldehyde) not having a hydroxyl group. Specifically, the phenolic trinuclear compound (A2) is produced by condensation reaction of one or two or more dialkyl-substituted phenol (c'1) represented by any of general formulae (c'1-1) to (c'1-4) below with a hydroxyl group-non-containing aromatic aldehyde (aromatic aldehyde not having a hydroxyl group) (c'2) represented by general formula (c'2) below.

[Chem. 5]

(c'1-1)
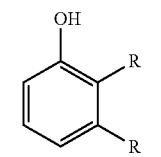

(c'1-2)
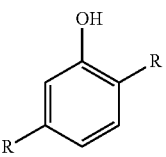

(c'1-3)
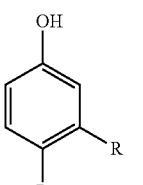

(c'1-4)
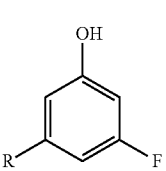

[Chem. 6]

(c'2)
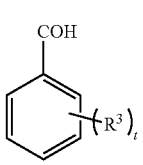

In the general formulae (c'1-1) to (c'1-4), R represents an alkyl group having 1 to 8 carbon atoms, which may have a substituent. The plurality of R present may be the same or different from each other, but are preferably the same. Examples of R include the same as those of "an alkyl group having 1 to 8 carbon atoms which may have a substituent" of $R^1$ and $R^2$ in the general formula (1).

In the general formula (c'2), $R^3$ represents an alkyl group having 1 to 8 carbon atoms, which may have a substituent. When a plurality of $R^3$ are present, they may be the same or different from each other. Examples of $R^3$ include the same as those of "an alkyl group having 1 to 8 carbon atoms which may have a substituent" of $R^1$ and $R^2$ in the general formula (1). In the general formula (c'2), t represents an integer of 0 to 5.

The phenolic trinuclear compound (A2) used in the present invention is preferably a condensate of one or two or more dialkyl-substituted phenols represented by any of the general formulae (c'1-1) to (c'1-4) with an aromatic aldehyde (benzaldehyde) which is the hydroxyl group-non-containing aromatic aldehyde represented by the general formula (c'2) in which t is 0, more preferably a condensate of one or two or more dialkyl-substituted phenols represented by the general formula (c'1-2) with benzaldehyde, even more preferably a condensate of one dialkyl-substituted phenol represented by the general formula (c'1-2) with benzaldehyde, and particularly preferably a compound produced by condensation reaction of 2,5-xylenol with benzaldehyde.

The condensation reaction of one or two or more dialkyl-substituted phenols (c'1) with the hydroxyl group-non-containing aromatic aldehyde (c'2) is performed under conditions which can employ a difference in reaction activation energy between carton atoms on an aromatic hydrocarbon group of the dialkyl-substituted phenol (c'1). Specifically, the phenolic trinuclear compound (A2) can be produced by, for example, polycondensation of the dialkyl-substituted phenol (c'1) with the hydroxyl group-non-containing aromatic aldehyde (c'2) in the presence of an acid catalyst.

The type of the acid catalyst, the use or non-use of the organic solvent, and the type of organic solvent used in condensation reaction of the dialkyl-substituted phenol (c'1) with the hydroxyl group-non-containing aromatic aldehyde (c'2), the reaction temperature, and the charging ratio [(c'1)/(c'2)] of the dialkyl-substituted phenol (c'1) to the hydroxyl group-non-containing aromatic aldehyde (c'2) are the same as the type of the acid catalyst, the use or non-use of the organic solvent, and the type of organic solvent used in condensation reaction of the dialkyl-substituted phenol (c1) with the hydroxyl group-containing aromatic aldehyde (c2), the reaction temperature, and the charging ratio [(c1)/(c2)].

Like the phenolic trinuclear compound (A1) produced by polymerization reaction, the phenolic trinuclear compound (A2) is preferably isolated and purified from the reaction solution (condensate) after polycondensation reaction before being used as a raw material (phenolic trinuclear compound (A)) of the novolac phenol resin according to the present invention. The purity of the phenolic trinuclear compound (A2) used as the phenolic trinuclear compound (A2) is preferably 85% or more, more preferably 90% or more, still more preferably 94% or more, and particularly preferably 98% or more. The purity of the phenolic trinuclear compound (A2) can be increased by the same method as for increasing the purity of the phenolic trinuclear compound (A1) by purification.

Examples of the phenolic trinuclear compound (A2) include compounds represented by general formulae (2-1) to (2-4) below. In the general formulae (2-1) to (2-4), t represents an integer of 0 to 5.

[Chem. 7]

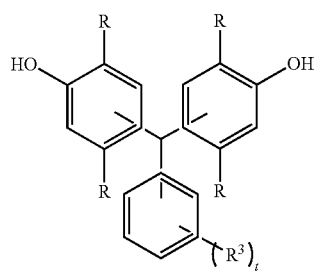

(2-1)

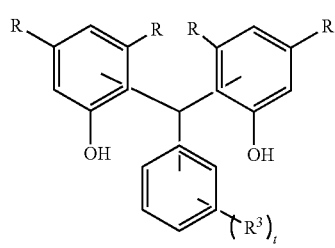

(2-2)

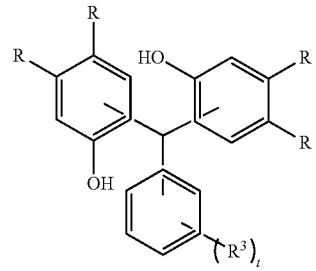

(2-3)

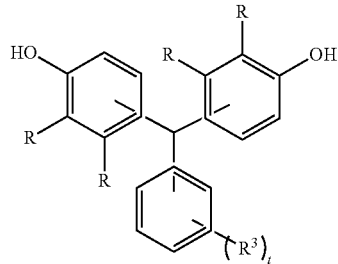

(2-4)

In the general formulae (2-1) to (2-4), R represents an alkyl group having 1 to 8 carbon atoms, which may have a substituent. The plurality of R present may be the same or different, but are preferably the same. Examples of R include the same as those of "an alkyl group having 1 to 8 carbon atoms which may have a substituent" of $R^1$ and $R^2$ in the general formula (1).

Also, in the general formulae (2-1) to (2-4), $R^3$ represents an alkyl group having 1 to 8 carbon atoms, which may have a substituent. When a plurality of $R^3$ are present, they may be the same or different. Examples of an alkyl group of $R^3$ include the same as those of "an alkyl group having 1 to 8 carbon atoms which may have a substituent" of $R^1$ and $R^2$ in the general formula (1).

Compounds represented by the general formulae (2-1) to (2-4) are preferably compounds in which R is a methyl group or an ethyl group and t is 0, and more preferably compounds in which R is a methyl group and t is 0.

Because a photosensitive composition which can produce a coating film having heat resistance and high resolution can be produced, the phenolic trinuclear compound (A2) is preferably a compound represented by the general formula (2-1), more preferably a compound represented by the general formula (2-1) in which Rs are each independently a methyl group or an ethyl group and t is 0, and even more preferably a compound represented by the general formula (2-1) in which R are all methyl groups and t is 0.

In addition, one or two or more phenolic trinuclear compounds (A1) and one or two or more phenolic trinuclear compound (A2) are used as the phenolic trinuclear compound (A) used as the raw material of the novolac phenol resin of the present invention. The molar ratio of the phenolic trinuclear compound (A1) to the phenolic trinuclear compound (A2) in the phenolic trinuclear compound (A) used as the raw material is 20:80 to 90:10. As the molar ratio of the phenolic trinuclear compound (A2) in the phenolic trinuclear compound (A) increases, the alkali developing property of the resultant novolac phenol resin decreases, and absorbance at exposure wavelengths of g-line, h-line, and i-line decreases, thereby increasing sensitivity. The molar ratio of the phenolic trinuclear compound (A1) to the phenolic trinuclear compound (A2) is more preferably 25:75 to 75:25.

The novolac phenol resin according to the present invention is produced by, for example, condensation of the phenolic trinuclear compound (A) with the aldehyde (B) in the presence of the acid catalyst. In producing the novolac phenol resin according to the present invention, preferably, the isolated and purified phenolic trinuclear compound (A1) is mixed with the phenolic trinuclear compound (A2) so that the molar ratio is 20:80 to 90:10, and condensation reaction of the resultant mixture with the aldehyde (B) is performed in the presence of the acid catalyst.

Examples of the aldehyde (B) used in the present invention include formaldehyde, paraformaldehyde, trioxane, acetaldehyde, propionaldehyde, polyoxymethylene, chloral, hexamethylenetetramine, furfural, glyoxal, n-butylaldehyde, caproaldehyde, allylaldehyde, benzaldehyde, crotonaldehyde, acrolein, tetraoxymethylene, phenylacetaldehyde, o-tolualdehyde, salicylaldehyde, and the like. These may be used alone or in combination of two or more. Among these, formaldehyde is preferred because of excellent reactivity, and formaldehyde may be used in combination with another aldehyde compound. When formaldehyde is used in combination with another aldehyde compound, the amount of other aldehyde compound used is preferably within a range of 0.05 to 1 mole relative to 1 mole of formaldehyde.

The charging ratio [(A)/(B)] of the phenolic trinuclear compound (A) to the aldehyde (B) in condensation reaction is preferably within a range of 1/0.5 to 1/1.2 and more preferably within a range of 1/0.6 to 1/0.9 in terms of molar ratio because an excessive increase in molecular weight (gelation) can be suppressed, and a phenolic resin for photoresist having a proper molecular weight can be produced.

Examples of the acid catalyst used in the reaction include inorganic acids such as sulfuric acid, hydrochloric acid, nitric acid, hydrobromic acid, perchloric acid, phosphoric acid, and the like; sulfonic acids such as p-toluenesulfonic acid, methanesulfonic acid, benzenesulfonic acid, and the like; organic acids such as oxalic acid, succinic acid, malonic acid, monochloroacetic acid, dichloroacetic acid, and the like; Lewis acids such as boron trifluoride, anhydrous aluminum chloride, zinc chloride, and the like. Among these, sulfuric acid or p-toluenesulfonic acid is preferred because strong acidity is exhibited and reaction of the phenolic trinuclear compound (A) with the aldehyde (B) is accelerated with high activity. The amount of the acid catalyst used is preferably within a range of 0.1 to 25% by mass relative to the total mass of the reaction raw materials.

If required, the condensation reaction of the phenolic trinuclear compound (A) with the aldehyde (B) may be performed in the presence of an organic solvent. Examples of the organic solvent include the same as the organic solvents which can be used in polycondensation of the dialkyl-substituted phenol (c1) with the hydroxyl group-containing aromatic aldehyde (c2). The organic solvents can be used alone or in combination of two or more. Because of excellent solubility of the resultant novolac phenol resin, 2-ethoxyethanol is preferred as the organic solvent.

The novolac phenol resin according to the present invention preferably has one or more structural parts selected from the group consisting of a structural part (I-1) represented by general formula (I-1) below and a structural part (II-1) represented by general formula (II-1) below, and more preferably has one or more structural parts selected from the group consisting of a structural part (I-1-1) represented by general formula (I-1-1) below and a structural part (II-1-1) represented by general formula (II-1-1) below. In the genera formulae (I-1) and (II-1), $R^1$ and $R^2$ are the same as in the general formula (1), and $R^4$ represents a hydrogen atom, an alkyl group which may have a substituent, or an aryl group which may have a substituent. Similarly, in the general formulae (I-1-1) and (II-1-1), $R^1$ and $R^2$ are the same as in the general formula (1).

[Chem. 8]

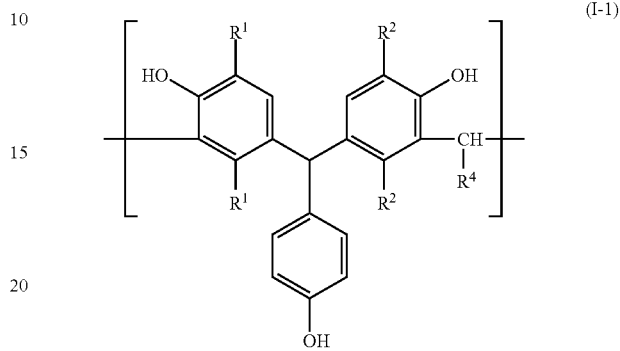

(I-1)

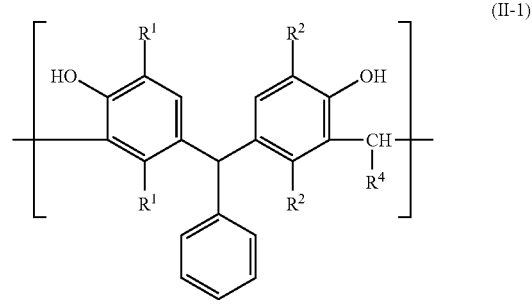

(II-1)

[Chem. 9]

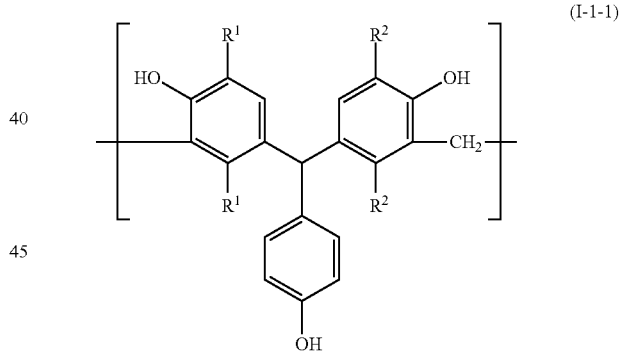

(I-1-1)

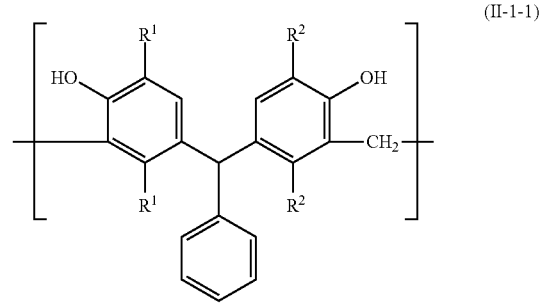

(II-1-1)

When $R^4$ in the general formulae (I-1) and (II-1) is an alkyl group which may have a substituent, the alkyl group may be linear or branched or may have a cyclic structure, but is preferably a linear group. In the present invention, when $R^4$ is an alkyl group, $R^4$ is preferably an alkyl group having 1 to 12 carbon atoms, more preferably an alkyl group having 1 to 8 carbon atoms, and still more preferably an alkyl group having 1 to 6 carbon atoms.

When $R^4$ in the general formulae (I-1) and (II-1) is an alkyl group, a hydrogen atom in the alkyl group may be substituted by a substituent. Examples of the substituent include a hydroxyl group, an alkoxy group having 1 to 6 carbon atoms, an aryl group which may have a substituent, a halogen atom, and the like. Examples of an alkoxy group having 1 to 6 carbon atoms and an aryl group include the same as the alkoxy groups and aryl groups exemplified as substituents which an alkyl group of $R^1$ or the like in the general formula (1) may have. The number of the hydrogen atoms which can be substituted is not particularly limited but is preferably 1 to 3 and more preferably 1 or 2. When an alkyl group has a plurality of substituents, the substituents may be the same or different from each other. Examples of an alkyl group of $R^4$ include a methyl group, an ethyl group, a propyl group, an isopropyl group, a n-butyl group, an isobutyl group, a tert-butyl group, a pentyl group, an isoamyl group, a hexyl group, a cyclohexyl group, a hydroxyethyl group, a hydroxypropyl group, a fluoromethyl group, a methoxyethyl group, an ethoxyethyl group, a methoxypropyl group, a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, a dihydroxynaphthylethyl group, and the like. Preferred are a methyl group, an ethyl group, a propyl group, an isopropyl group, a n-butyl group, an isobutyl group, a tert-butyl group, a pentyl group, an isoamyl group, a hexyl group, and a cyclohexyl group.

When $R^4$ in the general formulae (I-1) and (II-1) is an aryl group which may have a substituent, examples of the aryl group include a phenyl group, a naphthyl group, an indenyl group, a biphenyl group, and the like. Also, a hydrogen atom in the aryl group may be substituted by a substituent. Examples of the substituent include a hydroxyl group, an alkoxy group having 1 to 6 carbon atoms, an aryl group, a halogen atom, and the like. Examples of an alkoxy group having 1 to 6 carbon atoms and an aryl group include the same as the alkoxy groups and aryl groups exemplified as substituents which an alkyl group of $R^1$ or the like in the general formula (1) may have. The number of the hydrogen atoms which can be substituted is not particularly limited but is preferably 1 to 3 and more preferably 1 or 2. When an alkyl group has a plurality of substituents, the substituents may be the same or different from each other. Examples of an aryl group of $R^4$ which may have a substituent include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, a dihydroxynaphthyl group, a bromophenyl group, and the like.

The structural part represented by the general formula (I-1) or (II-1) is preferably a structural part in which $R^1$ and $R^2$ are the same group and $R^4$ is a hydrogen atom, more preferably a structural part in which $R^1$ and $R^2$ are the same unsubstituted alkyl group having 1 to 3 carbon atoms and $R^4$ is a hydrogen atom, and still more preferably a structural part in which both $R^1$ and $R^2$ are methyl groups and $R^4$ is a hydrogen atom.

The weight-average molecular weight of the novolac phenol resin according to the present invention is 1,000 to 35,000. In particular, the molecular weight of the novolac phenol resin having a structural unit represented by the general formula (I-1) or a structural unit represented by the general formula (II-1) as a repeating unit is preferably 5,000 to 100,000, more preferably 5,000 to 70,000, still more preferably 5,000 to 35,000, and particularly preferably 7,000 to 25,000 in terms of weight-average molecular weight (Mw) because a positive photoresist composition having excellent heat resistance and sensitivity can be produced.

In the present invention and the description, the weight-average molecular weight (Mw) and number-average molecular weight (Mn) of the novolac phenol resin were measured by using gel permeation chromatography (hereinafter, abbreviated as "GPC") under measurement conditions described below.

[Conditions for GPC Measurement]

Measuring apparatus: "HLC-8220 GPC" manufactured by Tosoh Corporation

Column: "Shodex KF802" (8.0 mm I. D.×300 mm) manufactured by Showa Denko K. K.+"Shodex KF802" (8.0 mm I. D.×300 mm) manufactured by Showa Denko K. K.+"Shodex KF803" (8.0 mm I. D.×300 mm) manufactured by Showa Denko K. K.+"Shodex KF804" (8.0 mm I. D.×300 mm) manufactured by Showa Denko K. K.

Column temperature: 40° C.

Detector: RI (differential refractometer)

Data processing: "GPC-8020 model II version 4.30" manufactured by Tosoh Corporation Developing solvent: tetrahydrofuran Flow rate: 1.0 mL/min Sample: prepared by filtering a 0.5 mass % tetrahydrofuran solution in terms of resin solid content with a microfilter.

Injection amount: 0.1 mL

Standard sample: monodisperse polystyrene described below.

(Standard sample: monodisperse polystyrene)

"A-500" manufactured by Tosoh Corporation

"A-2500" manufactured by Tosoh Corporation

"A-5000" manufactured by Tosoh Corporation

"F-1" manufactured by Tosoh Corporation

"F-2" manufactured by Tosoh Corporation

"F-4" manufactured by Tosoh Corporation

"F-10" manufactured by Tosoh Corporation

"F-20" manufactured by Tosoh Corporation

The novolac phenol resin according to the present invention has excellent heat resistance due to having a large number of benzene rings and also has high alkali solubility due to a relatively high content of hydroxyl group. Further, the novolac phenol resin has low absorbance at the exposure wavelengths of g-line, h-line, and i-line. Therefore, the photosensitive composition containing the novolac phenol resin according to the present invention is suitable as a resist material and is particularly suitable as a resist material for a thick resist (for example, a resist for forming a pattern from a resist coating film having a thickness of 2 μm or more). The photosensitive composition containing the novolac phenol resin according to the present invention can form a resist coating film having excellent heat resistance and alkali developability and satisfactory sensitivity even when the thickness of the coating film is increased.

The novolac phenol resin produced by mixing the novolac phenol resin (A1), which is produced by reacting the phenolic trinuclear compound (A1) with the aldehyde (B) under the acid catalyst, with the novolac phenol resin (A2), which is produced by reacting the phenolic trinuclear compound (A2) with the aldehyde (B) under the acid catalyst, has high heat resistance and alkali solubility and has a low ratio of the structural unit derived from condensation reaction of the phenolic trinuclear compound (A1) and the aldehyde (B) in the whole resin and also has low absorbance at the exposure wavelengths of g-line, h-line, and i-line as compared with a resin containing only the novolac phenol resin (A1). Therefore, like the photosensitive composition containing the novolac phenol resin according to the present invention, the photosensitive composition containing the novolac phenol resin (A1) and the novolac phenol resin (A2) can form a coating film having excellent heat resistance and alkali developability and satisfactory sensitivity even when the thickness of the coating film is increased.

The content ratio of the novolac phenol resin (A1) to the novolac phenol resin (A2) in the photosensitive composition containing the novolac phenol resin (A1) and the novolac phenol resin (A2) is preferably 20:80 to 90:10, more preferably 25:75 to 90:10, and still more preferably 25:75 to 75:25 in terms of molar ratio of the structural unit derived from condensation reaction of the phenolic trinuclear compound (A1) with the aldehyde (B) to the structural unit derived from condensation reaction of the phenolic trinuclear compound (A2) with the aldehyde (B) in the photosensitive composition.

The condensation reaction of the phenolic trinuclear compound (A1) with the aldehyde (B) and the condensation reaction of the phenolic trinuclear compound (A2) with the aldehyde (B) can be performed by the same method as the condensation reaction of the phenolic trinuclear compound (A) with the aldehyde (B) described above.

The photosensitive composition according to the present invention (including both the photosensitive composition containing the novolac phenol resin according to the present invention and the photosensitive composition containing the novolac phenol resin (A1) and the novolac phenol resin (A2)) may further contain another alkali-soluble resin. Any alkali-soluble resin ca be used as the other alkali-soluble resin as long as it is soluble in an alkali developer or is dissolved in an alkali developer by being used in combination with an additive such as a photoacid generator or the like.

Examples of the other alkali-soluble resin used include phenolic hydroxyl group-containing resins other than the novolac phenol resin according to the present invention, homopolymers or copolymers of hydroxyl group-containing styrene compounds such as p-hydroxystyrene, p-(1,1,1,3,3,3-hexafluoro-2-hydroxypropyl)styrene, and the like, resins produced by modifying the hydroxyl group with an acid decomposable group such as a carbonyl group, a benzyloxycarbonyl group, or the like, homopolymers or copolymers of (meth)acrylic acid, alternating polymers of a polymerizable monomer such as a norbornene compound, a tetracyclododecene compound, or the like and maleic anhydride or maleimide, and the like.

Examples of phenolic hydroxyl group-containing resins other than the novolac phenol resin according to the present invention include phenol resins such as phenol novolac resins, cresol novolac resins, naphthol novolac resins, co-condensed novolac resins using various phenolic compounds, aromatic hydrocarbon formaldehyde resin-modified phenol resins, dicyclopentadiene phenol-added resins, phenol aralkyl resins (Zylock resins), naphthol aralkyl resins, trimethylolmethane resins, tetraphenylolethane resins, biphenyl-modified phenol resins (polyhydric phenol compounds in which phenol nuclei are connected through a bismethylene group), biphenyl-modified naphthol resins (polyhydric naphthol compounds in which phenol nuclei are connected through a bismethylene group), aminotriazine-modified phenol resins (polyhydric phenol compounds in which phenol nuclei are connected through melamine, benzoguanamine, or the like), alkoxy group-containing aromatic ring-modified novolac resins (polyhydric phenol compounds in which a phenol nucleus and an alkoxy group-containing aromatic ring are connected through formaldehyde), and the like.

Among the other phenolic hydroxyl group-containing resins, cresol novolac resins or co-condensed novolac resins of cresol and other phenolic compounds are preferred. Specifically, the cresol novolac resins or co-condensed novolac resins of cresol and other phenolic compounds are novolac resins produced by using at least one cresol selected from the group consisting of o-cresol, m-cresol, and p-cresol, and aldehyde as essential raw materials, and properly using another phenolic compound in combination with the cresol.

Examples of the other phenolic compound include phenol; xylenol such as 2,3-xylenol, 2,4-xylenol, 2,5-xylenol, 2,6-xylenol, 3,4-xylenol, 3,5-xylenol, and the like; ethylphenol such as o-ethylphenol, m-ethylphenol, p-ethylphenol, and the like; isopropylphenol, butylphenol such as butylphenol, p-tert-butylphenol, and the like; alkylphenol such as p-pentylphenol, p-octylphenol, p-nonylphenol, p-cumylphenol, and the like; halogenated phenol such as fluorophenol, chlorophenol, bromophenol, idophenol, and the like; mono-substituted phenol such as p-phenylphenol, aminophenol, nitrophenol, dinitrophenol, trinitrophenol, and the like; condensed polycyclic phenol such as 1-naphthol, 2-naphthol, and the like; polyhydric phenol such as resorcin, alkylresorcin, pyrogallol, catechol, alkylcatechol, hydroquinone, alkylhydroquinone, fluoroglucine, bisphenol A, bisphenol F, bisphenol S, dihydroxynaphthaline, and the like. These other phenolic compounds may be used alone or in combination of two or more. When the other phenolic compound is used, the amount of the other phenolic compound used is preferably a ratio within a range of 0.05 to 1 mole relative to a total of 1 mole of cresol raw materials.

Examples of the aldehyde used for producing the cresol novolac resins or co-condensed novolac resins of cresol and other phenolic compounds include the aldehydes described above. The aldehydes may be used alone or in combination of two or more. In particular, formaldehyde is preferred because of excellent reactivity, and another aldehyde compound may be used in combination with formaldehyde. When another aldehyde compound is used in combination with formaldehyde, the amount of other aldehyde compound used is preferably within a range of 0.05 to 1 mole relative to 1 mole of formaldehyde.

With respect to the reaction ratio between the phenolic compound and the aldehyde for producing the novolac resin, the amount of the aldehyde is preferably within a range of 0.3 to 1.6 moles and more preferably within a range of 0.5 to 1.3 moles relative to 1 mole of the phenolic compound because the photosensitive composition having excellent sensitivity and heat resistance can be produced.

The reaction of the phenolic compound with the aldehyde can be performed by, for example, a method including performing reaction at a temperature condition of 60° C. to 140° C. in the presence of an acid catalyst and then removing water and remaining monomers under a reduced-pressure condition. Examples of the acid catalyst used include oxalic acid, sulfuric acid, hydrochloric acid, phenolsulfonic acid, para-toluenesulfonic acid, zinc acetate, manganese acetate, and the like. These may be used alone or in combination of two or more. Among these, oxalic acid is preferred in view of excellent catalyst activity.

Among the cresol novolac resins or condensed novolac resins of cresol and other phenolic compounds described in detail above, a cresol novolac resin using only meta-cresol or a cresol novolac resin using combination of meta-cresol and para-cresol is preferred. Also, in the latter resin, the reaction molar ratio [metacresol/paracresol] of metacresol to paracresol is preferably within a range of 10/0 to 2/8 and more preferably within a range of 7/3 to 2/8 because the photosensitive composition having an excellent balance between sensitivity and heat resistance can be produced.

When the other alkali-soluble resin is used, the mixing ratio of the novolac phenol resin according to the present invention to the other alkali-soluble resin can be arbitrarily adjusted according to desired application. In particular, because the effect of the present invention is satisfactorily exhibited, the novolac phenol resin according to the present invention is preferably used in an amount of 60% by mass or more, more preferably 80% by mass or more, relative to the total of the novolac phenol resin according to the present invention and the other alkali-soluble resin.

The photosensitive composition according to the present invention preferably contains the novolac phenol resin according to the present invention and an organic solvent. The novolac phenol resin according to the present invention is more preferably a solution prepared by dissolving in an organic solvent. Examples of the organic solvent include ethylene glycol alkyl ethers such as ethylene glycol monomethyl ether, ethylene glycol monoethyl ether, ethylene glycol monopropyl ether, ethylene glycol monobutyl ether, and the like; diethylene glycol dialkyl ethers such as diethylene glycol dimethyl ether, diethylene glycol diethyl ether, diethylene glycol dipropyl ether, diethylene glycol dibutyl ether, and the like; ethylene glycol alkyl ether acetates such as methyl cellosolve acetate, ethyl cellosolve acetate, and the like; propylene glycol alkyl ether acetates such as propylene glycol monomethyl ether acetate, propylene glycol monoethyl ether acetate, propylene glycol monopropyl ether acetate, and the like; ketones such as acetone, methyl ethyl ketone, cyclohexanone, methyl amyl ketone, and the like; cyclic ethers such as dioxane and the like; esters such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, ethyl acetoacetate, and the like. These organic solvents can be used alone or in combination of two or more.

The photosensitive composition according to the present invention may further contain a photosensitizer used for general resist materials. The photosensitizer used is, for example, a compound having a quinone diazide group. Examples of the compound having a quinone diazide group include complete ester compounds, partial ester compounds, amidated products, partially amidated products, and the like of aromatic (poly)hydroxycompounds with sulfonic acid having a quinone diazide group, such as naphthoquinone-1,2-diazide-5-sulfonic acid, naphthoquinone-1,2-diazide-4-sulfonic acid, ortho-anthraquinone diazide sulfonic acid, or the like.

Examples of the aromatic (poly)hydroxycompounds used include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, 2,3,3',4,4',5'-hexahydroxybenzophenone, and the like;

bis[(poly)hydroxyphenyl]alkane compounds such as bis(2,4-dihydroxyphenyl)methane, bis(2,3,4-trihydroxyphenyl)methane, 2-(4-hydroxyphenyl)-2-(4'-hydroxyphenyl)propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-{1-[4-[2-(4-hydroxyphenyl)-2-propyl]phenyl]ethylidene}bisphenol, 3,3'-dimethyl-{1-[4-[2-(3-methyl-4-hydroxyphenyl)-2-propyl]phenyl]ethylidene}bisphenol, and the like;

tris(hydroxyphenyl)methane compounds or methyl-substituted compounds thereof, such as tris(4-hydroxyphenyl)methane, bis(4-hydroxy-3,5-dimethylphenyl)-4-hydroxyphenylmethane, bis(4-hydroxy-2,5-dimethylphenyl)-4-hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-2,5-dimethylphenyl)-3,4-dihydroxyphenylmethane, bis(4-hydroxy-3,5-dimethylphenyl)-3,4-dihydroxyphenylmethane, and the like; and bis(cyclohexylhydroxyphenyl)(hydroxyphenyl)methane compounds or methyl-substituted compounds thereof such as bis(3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(5-cyclohexyl-4-hydroxy-2-methylphenyl)-2-hydroxyphenylmethane, bis(5-cyclohexyl-4-hydroxy-2-methylphenyl)-3-hydroxyphenylmethane, bis(5-cyclohexyl-4-hydroxy-2-methylphenyl)-4-hydroxyphenylmethane, bis(3-cyclohexyl-2-hydroxyphenyl)-3-hydroxyphenylmethane, bis(5-cyclohexyl-4-hydroxy-3-methylphenyl)-4-hydroxyphenylmethane, bis(5-cyclohexyl-4-hydroxy-3-methylphenyl)-3-hydroxyphenylmethane, bis(5-cyclohexyl-4-hydroxy-3-methylphenyl)-2-hydroxyphenylmethane, bis(3-cyclohexyl-2-hydroxyphenyl)-4-hydroxyphenylmethane, bis(3-cyclohexyl-2-hydroxyphenyl)-2-hydroxyphenylmethane, bis(5-cyclohexyl-2-hydroxy-4-methylphenyl)-2-hydroxyphenylmethane, bis(5-cyclohexyl-2-hydroxy-4-methylphenyl)-4-hydroxyphenylmethane, and the like. These photosensitizers may be used alone or in combination of two or more.

When the photosensitizer is used, because the composition having excellent photosensitivity can be produced, the mixing amount is preferably within a range of 5 to 50 parts by mass relative to 100 parts by mass of the resin solid in the photosensitive composition according to the present invention.

The photosensitive composition according to the present invention may contain a surfactant for the purpose of improving film formability and adhesion of a pattern and decreasing development defects when used in resist applications. Examples of the surfactant used include nonionic surfactants, such as polyoxyethylene alkyl ether compounds such as polyoxyethylene lauryl ether, polyoxyethylene stearyl ether, polyoxyethylene cetyl ether, polyoxyethylene oleyl ether, and the like; polyoxyethylene alkylaryl ether compounds such as polyoxyethylene octylphenol ether, polyoxyethylene nonylphenol ether, and the like; polyoxyethylene-polyoxypropylene copolymers, sorbitan fatty acid ester compounds such as sorbitan monolaurate, sorbitan monopalmitate, sorbitan monostearate, sorbitan monooleate, sorbitan trioleate, sorbitan tristearate, and the like; polyoxyethylene sorbitan fatty acid ester compounds such as polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate, and the like; fluorine-based surfactants each having a fluorine atom in the molecular structure, such as a copolymer of a polymerizable monomer having a fluoroaliphatic group and [poly(oxyalkylene](meth)acrylate, and the like; silicone-based surfactants each having a silicone structural part in the molecular structure, and the like. These may be used alone or in combination of two or more.

The mixing amount of the surfactant is preferably within a range of 0.001 to 2 parts by mass relative to 100 parts by mass of the resin solid content in the photosensitive composition according to the present invention.

The photosensitive composition according to the preset invention may further contain a curing agent. When the photosensitive composition according to the present invention contains the curing agent, the photosensitive composition may contain one curing agent or two or more curing agents.

Examples of the curing agent which may be contained in the photosensitive composition according to the present invention include a melamine compound substituted by at least one group selected from a methylol group, an alkoxymethyl group, and an acyloxymethyl group, a guanamine compound, a glycoluril compound, an urea compound, a resole resin, an epoxy compound, an isocyanate compound, an azide compound, a compound containing a double bond such as an alkenyl ether group or the like, an acid anhydride, an oxazoline compound, and the like.

Examples of the melamine compound include hexamethylolmelamine, hexamethoxymethylmelamine, a compound produced by methoxymethylating 1 to 6 methylol groups of hexamethylolmelamine, hexamethoxyethylmelamine, hexaacyloxymethylmelamine, a compound produced by acyloxymethylating 1 to 6 methylol groups of hexamethylolmelamine, and the like.

Examples of the guanamine compound include tetramethylolguanamine, tetramethoxymethylguanamine, tatramethoxymethylbenzoguanamine, a compound produced by methoxymethylating 1 to 4 methylol groups of tetramethylolguanamine, tetramethoxyethylguanamine, tetraacyloxyguanamine, a compound produced by acyloxymethylating 1 to 4 methylol groups of tetramethylolguanamine, and the like.

Examples of the glycoluril compound include 1,3,4,6-tetrakis(methoxymethyl) glycoluril, 1,3,4,6-tetrakis(butoxymethyl) glycoluril, 1,3,4,6-tetrakis(hydroxymethyl) glycoluril, and the like.

Examples of the urea compound include 1,3-bis(hydroxymethyl)urea, 1,1,3,3-tetrakis(butoxymethyl)urea, 1,1,3,3-tetrakis(methoxymethyl)urea, and the like.

Examples of the resole resin include polymers each produced by reacting a phenolic hydroxyl group-containing compound such as alkyl phenol, such as phenol, cresol, xylenol, or the like, phenylphenol, resolcinol, biphenyl, bisphenol such as bisphenol A, bisphenol F, or the like, naphthol, dihydroxynaphthalene, or the like, with an aldehyde compound under the condition of an alkaline catalyst.

Examples of the epoxy compound include tris(2,3-epoxypropyl) isocyanurate, trimethylolmethane triglycidyl ether, trimethylolpropane triglycidyl ether, triethylolethane triglycidyl ether, and the like.

Examples of the isocyanate compound include tolylene diisocyanate, diphenylmethane diisocyanate, hexamethylene diisocyanate, cyclohexane diisocyanate, and the like.

Examples of the azide compound include 1,1'-biphenyl-4,4'-bisazide, 4,4'-methylidene bisazide, 4,4'-oxybisazide, and the like.

Examples of the compound containing a double bond such as an alkenyl ether group or the like include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, trimethylolpropane trivinyl ether, and the like.

Examples of the acid anhydride include aromatic acid anhydrides such as phthalic anhydride, trimellitic anhydride, pyromellitic anhydride, 3,3',4,4' benzophenone tetracarboxylic dianhydride, biphenyltetracarboxylic dianhydride, 4,4'-(isopropylidene)diphthalic anhydride, 4,4'-(hexafluoroisopropylidene)diphthalic anhydride, and the like; alicyclic carboxylic acid anhydrides such as tetrahydrophthalic anhydride, methyltetrahydrophthalic anhydride, hexahydrophthalic anhydride, methylhexahydrophthalic anhydride, endo-methylenetetrahydrophthalic anhydride, dodecenylsuccinic anhydride, trialkyltetrahydrophthalic anhydride, and the like.

Among these, the glycoluril compound, the urea compound, and the resole resin are preferred, and the glycoluril compound is particularly preferred because the composition having excellent curability and more excellent thermal decomposition resistance is produced.

When the photosensitive compound according to the present invention contains the curing agent, the amount of the curing agent mixed is preferably a ratio of 0.1 to 50 parts by mass, more preferably a ratio of 0.1 to 30 parts by mass, and still more preferably a ratio of 0.5 to 20 parts by mass relative to 100 parts by mass of the novolac phenol resin according to the present invention.

The photosensitive composition according to the present invention may further contain a photoacid generator. When the photosensitive composition according to the present invention contains a photoacid generator, the photosensitive composition may contain one photoacid generator or two or more photoacid generators.

Examples of the photoacid generator include organic halogen compounds, sulfonic acid esters, onium salts, diazonium salts, disulfone compounds, and the like. These may be used alone or in combination of two or more. Specific examples thereof include haloalkyl group-containing-s-triazine derivatives such as tris(trichloromethyl)-s-triazine, tris(tribromomethyl-s-triazine, tris(dibromomethyl)-s-triazine, 2,4-bis(tribromomethyl)-6-p-methoxyphenyl-s-triazine, and the like;

halogen-substituted paraffin hydrocarbon compounds such as 1,2,3,4-tetrabromobutane, 1,1,2,2-tetrabromoethane, carbon tetrabromide, iodoform, and the like; halogen-substituted cycloparaffin hydrocarbon compounds such as hexabromocyclohexane, hexachlorocyclohexane, hexabromocyclododecane, and the like;

haloalkyl group-containing benzene derivatives such as bis(trichloromethyl)benzene, bis(tribromomethyl)benzene, and the like; haloalkyl group-containing sulfone compounds such as tribromomethylphenylsulfone, trichloromethylphenylsulfone, and the like; halogen-containing sulfolane compounds such as 2,3-dibromosulfolane and the like; haloalkyl group-containing isocyanurate compounds such as tris(2,3-dibromopropyl)isocyanurate and the like;

sulfonium salts such as triphenylsulfonium chloride, triphenylsulfonium methane sulfonate, triphenylsulfonium trifluoromethane sulfonate, triphenylsulfonium p-toluenesulfonate, triphenylsulfonium tetrafluoroborate, triphenylsulfonium hexafluoroarsenate, triphenylsulfonium hexafluorophosphonate, and the like;

iodonium salts such as diphenyliodonium trifluoromethane sulfonate, diphenyliodonium p-toluenesulfonate, diphenyliodonium tetrafluoroborate, diphenyliodonium hexafluoroarsenate, diphenyliodonium hexafluorophosphonate, and the like;

sulfonic acid ester compounds such as methyl p-toluenesulfonate, ethyl p-toluenesulfonate, butyl p-toluenesulfonate, phenyl p-toluenesulfonate, 1,2,3-tris(p-toluenesulfonyloxy) benzene, p-toluenesulfonic acid benzoin ester, methyl methanesulfonate, ethyl methanesulfonate, butyl methanesulfonate, 1,2,3-tris(methanesulfonyloxy)benzene, phenyl methanesulfonate, methanesulfonic acid benzoin ester, methyl trifluromethanesulfonate, ethyl trifluoromethanesulfonate, butyl trifluoromethanesulfonate, 1,2,3-tris(trifluoromethanesulfonyloxy)benzene, phenyl trifluoromethanesulfonate, trifluoromethanesulfonic acid benzoin ester, and the like; disulfone compounds such as diphenyl disulfone and the like;

sulfone diazide compounds such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomethane, cyclopentylsulfonyl-(2-methoxyphenylsulfonyl)diazomethane, cyclopentylsulfonyl-(3-methoxyphenylsulfonyl)diazomethane, cyclopentylsulfonyl-(4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl)diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl)diazomethane, cyclopentylsulfonyl-(3-chlorophenylsulfonyl)diazomethane, cyclopentylsulfonyl-(4-chlorophenylsulfonyl)diazomethane, cyclohexylsulfonyl-(2-trifluoromethylphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl)diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-trimethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl-(2,3,4-triethylphenylsulfonyl)diazomethane, phenylsulfonyl-(2-methoxyphenylsulfonyl)diazomethane, phenylsulfonyl-(3-methoxyphenylsulfonyl)diazomethane, phenylsulfonyl-(4-methoxyphenylsulfonyl)diazomethane, bis(2-methoxyphenylsulfonyl)diazomethane, bis(3-methoxyphenylsulfonyl)diazomethane, bis(4-methoxyphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl)diazomethane, phenylsulfonyl-(2,3,4-triethylphenylsulfonyl)diazomethane, 2,4-dimethylphenylsulfonyl-(2,4,6-trimethylphenylsulfonyl)diazomethane, 2,4-dimethylphenylsulfonyl-(2,3,4-trimethylphenylsulfonyl)diazomethane, phenylsulfonyl-(2-fluorophenylsulfonyl)diazomethane, phenylsulfonyl-(3-fluorophenylsulfonyl)diazomethane, phenylsulfonyl-(4-fluorophenylsulfonyl)diazomethane, and the like;

o-nitrobenzylester compounds such as o-nitrobenzyl-p-toluenesulfonate and the like; and sulfone hydrazide compounds such as N,N'-di(phenylsulfonyl)hydrazide and the like.

The amount of the photoacid generator added is preferably within a range of 0.1 to 20 parts by mass relative to 100 parts by mass of the resin solid content in the photosensitive composition according to the present invention because the photosensitive composition has high photosensitivity.

The photosensitive composition according to the present invention may contain an organic basic compound for neutralizing the acid produced from the photoacid generator during exposure. Adding the organic basic compound has the effect of preventing a dimensional variation of a resist pattern due to the movement of the aid produced from the photoacid generator. The organic basic compound used is, for example, an organic amine compound selected from nitrogen-containing compounds. Examples thereof include pyrimidine compounds such as pyrimidine, 2-aminopyrimidine, 4-aminopyrimidine, 5-aminopyrimidine, 2,4-diaminopyrimidine, 2,5-diaminopyrimidine, 4,5-diaminopyrimidine, 4,6-diaminopyrimidine, 2,4,5-triaminopyrimidine, 2,4,6-triaminopyrimidine, 4,5,6-triaminopyrimidine, 2,4,5,6-tetraaminopyrimidine, 2-hydroxypyrimidine, 4-hydroxypyrimidine, 5-hydroxypyrimidine, 2,4-dihydroxypyrimidine, 2,5-dihydroxypyrimidine, 4,5-dihydroxypyrimidine, 4,6-dihydroxypyrimidine, 2,4,5-trihydroxypyrimidine, 2,4,6-trihydroxypyrimidine, 4,5,6-trihydroxypyrimidine, 2,4,5,6-tetrahydroxypyrimidine, 2-amino-4-hydroxypyrimidine, 2-amino-5-hydroxypyrimidine, 2-amino-4,5-dihydroxypyrimidine, 2-amino-4,6-dihydroxypyrimidine, 4-amino-2,5-dihydroxypyrimidine, 4-amino-2,6-dihydroxypyrimidine, 2-amino-4-methylpyrimidine, 2-amino-5-methylpyrimidine, 2-amino-4,5-dimethylpyrimidine, 2-amino-4,6-dimethylpyrimidine, 4-amino-2,5-dimethylpyrimidine, 4-amino-2,6-dimethylpyrimidine, 2-amino-4-methoxypyrimidine, 2-amino-5-methoxypyrimidine, 2-amino-4,5-dimethoxypyrimidine, 2-amino-4,6-dimethoxypyrimidine, 4-amino-2, 5-dimethoxypyrimidine, 4-amino-2,6-dimethoxypyrimidine, 2-hydroxy-4-methylpyrimidine, 2-hydroxy-5-methylpyrimidine, 2-hydroxy-4,5-dimethylpyrimidine, 2-hydroxy-4,6-dimethylpyrimidine, 4-hydroxy-2,5-dimethylpyrimidine, 4-hydroxy-2,6-dimethylpyrimidine, 2-hydroxy-4-methoxypyrimidine, 2-hydroxy-4-methoxypyrimidine, 2-hydroxy-5-methoxypyrimidine, 2-hydroxy-4,5-dimethoxypyrimidine, 2-hydroxy-4,6-dimethoxypyrimidine, 4-hydroxy-2,5-dimethoxypyrimidine, 4-hydroxy-2,6-dimethoxypyrimidine, and the like;

pyridine compounds such as pyridine, 4-dimethylaminopyridine, 2,6-dimethylpyridine, and the like;

amine compounds substituted by a hydroxyalkyl group having 1 or more and 4 or less carbon atoms, such as diethanolamine, triethanolamine, triisopropanolamine, tris(hydroxymethyl)aminomethane, bis(2-hydroxyethyl)imino tris(hydroxymethyl)methane, and the like; and aminophenol compounds such as 2-aminophenol, 3-aminophenol, 4-aminophenol, and the like. These may be used alone or in combination of two or more. Among these, the pyrimidine compounds, pyridine compounds, or amine compounds having a hydroxyl group are preferred, and the amine compounds having a hydroxyl group are particularly preferred because of excellent dimensional stability of a resist pattern after exposure.

When the organic basic compound is added to the photosensitive composition according to the present invention, the adding amount is preferably within in a range of 0.1 to 100 mol % and more preferably within a range of 1 to 50 mol % relative to the content of the photoacid generator.

The photosensitive composition according to the present invention may further contain a filler. The filler can further improve the hardness and heat resistance of a coating film. The filler contained in the photosensitive composition according to the present invention may be an organic filler but is preferably an inorganic filler. Examples of the inorganic filler include silica, mica, talc, clay, bentonite, montmorillonite, kaolinite, wollastonite, calcium carbonate, calcium hydroxide, magnesium carbonate, titanium oxide, alumina, aluminum hydroxide, barium sulfate, barium titanate, potassium titanate, zinc oxide, glass fibers, and the like. Among these, silica is preferably used because the thermal expansion coefficient can be decreased.

The photosensitive composition according to the present invention is preferably a solution or dispersion prepared by dissolving or dispersing, besides the novolac phenol resin according to the present invention, if required, other various additives such as another resin, a photosensitizer, a surfactant, a curing agent, a photoacid generator, a filler, an organic basic compound, a dye, a pigment, a dissolution accelerator, etc. in an organic solvent. A coating film can be formed by applying an organic solvent solution or the like on a substrate or the like. The dye, pigment, and dissolution accelerator used can be properly selected from those generally used as additives for resist materials in view of use application or the like.

The photosensitive composition according to the present invention can be prepared by mixing the components described above by using a stirrer or the like. When the photosensitive composition contains the filler and the pigment, the composition can be prepared by dispersing or mixing using a disperser such as a dissolver, a homogenizer, a three-roll mill, or the like.

The photosensitive composition according to the present invention may be also used as a resist material. The photosensitive composition according to the present invention may be used directly as a resist solution in a state of being dissolved or dispersed in an organic solvent or used as a resist film formed by applying an organic solvent solution or dispersion in the form of film and then removing the solvent. Examples of a support film used for the resist film include films of synthetic resins such as polyethylene, polypropylene, polycarbonate, polyethylene terephthalate, and the like, and the film may include a single layer or a plurality of laminated layers. Also, a surface of the support film may be a corona treated-surface or a surface to which a release agent is applied.

A photolithography method using the resist material including the photosensitive composition according to the present invention includes, for example, applying the resist material on an object of silicon substrate photolithography and then prebaking the resist material under a temperature condition of 60° C. to 150° C. In this method, an application method may be any one of the methods such as spin coating, roll coating, flow coating, dip coating, spray coating, doctor blade coating, and the like. In next forming a resist pattern, when the resist material is a positive type, an intended resist pattern is exposed to light through a predetermined mask, and exposed portions are dissolved with an alkali developer to form the resist pattern.

Examples of an exposure light source include infrared light, visible light, ultraviolet light, far-ultraviolet light, X-rays, electron beams, and the like. Examples of ultraviolet light include g-line (wavelength of 436 nm), K-line (wavelength of 405 nm), i-line (wavelength of 365 nm), KrF excimer laser (wavelength of 248 nm), ArF excimer laser (wavelength of 193 nm), F2 excimer laser (wavelength of 157 nm), EUV laser (wavelength of 13.5 nm), and the like. The photosensitive composition according to the present invention has low absorbance at these exposure wavelengths and thus can form a resist pattern with high sensitivity and high resolution even by using any one of the light sources.

Further, the photosensitive composition according to the present invention has excellent heat resistance and thus, a thin film (for example, a resist coating film) including the photosensitive composition containing the novolac phenol resin according to the present invention as a main component is suitable as a permanent film remaining also in the final product after the resist pattern is formed according to demand. In a product having a gap between members, distortion may occur due to a difference in thermal expansion between the member side and the gap side of the permanent film. However, the permanent film including the photosensitive composition containing the novolac phenol resin according to the present invention as a main component has the excellent property of little causing such distortion.

The permanent film represents a coating film which includes a photosensitive composition and is formed on a part or between parts constituting a product in a semiconductor device such as IC, LSI, or the like, a display device such as a thin display or the like, and which also remains after the completion of the product. Examples of the permanent film include semiconductor device-related permanents films such as a solder resist, a packaging material, an underfill material, a package adhesive layer of a circuit element or the like, and an adhesive layer between an integrated circuit element and a circuit board, and thin display-related permanent films for LCD, OELD, and the like, such as a thin-film transistor protecting film, a liquid crystal color filter protecting film, a black matrix, a spacer, and the like.

EXAMPLES

The present invention is described in further detail below by giving examples, but the present invention is not limited to these examples. Hereinafter, "parts" and "%" are on a mass basis unless otherwise specified.

<GPC Measurement of Resin>

The molecular weight distribution of a resin was measured by GPC according to a polystyrene standard method under measurement conditions described below.

(GPC Measurement Conditions)

Measuring apparatus: "HLC-8220 GPC" manufactured by Tosoh Corporation

Column: "Shodex KF802" (8.0 mm I. D.×300 mm) manufactured by Showa Denko K. K.+"Shodex KF802" (8.0 mm I. D.×300 mm) manufactured by Showa Denko K. K.+"Shodex KF803" (8.0 mm I. D.×300 mm) manufactured by Showa Denko K. K.+"Shodex KF804" (8.0 mm I. D.×300 mm) manufactured by Showa Denko K. K.

Detector: RI (differential refractometer)

Measurement conditions:

Column temperature: 40° C.

Developing solvent: tetrahydrofuran (THF)

Flow rate: 1.0 mL/min

Sample: prepared by filtering a 1.0 mass % tetrahydrofuran solution in terms of resin solid content with a microfilter (5 μL).

Data processing: "GPC-8020 model II data analysis version 4.30" manufactured by Tosoh Corporation Standard sample: monodisperse polystyrene with a known molecular weight described below according to the measurement manual of "GPC-8020 model II data analysis version 4.30" was used.

(Monodisperse Polystyrene)

"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation
"F-550" manufactured by Tosoh Corporation <$^{13}$C-NMR Spectrum Measurement of Resin>

A $^{13}$C-NMR spectrum of a resin was measured by using "JNM-LA300" manufactured by JEOL Ltd., and the structure was analyzed by analyzing a DMSO-$d_6$ solution of a sample. The measurement conditions for the $^{13}$C-NMR spectrum are shown below.

<Conditions for $^{13}$C-NMR Spectrum Measurement>

Measurement mode: SGNNE (NOE-suppressed 1H complete decoupling method)

Pulse angle: 45° C. pulse

Sample concentration: 30 wt %

Cumulative number: 10000

Synthesis Example 1

Synthesis of Phenolic Trinuclear Compound

Figure 2:
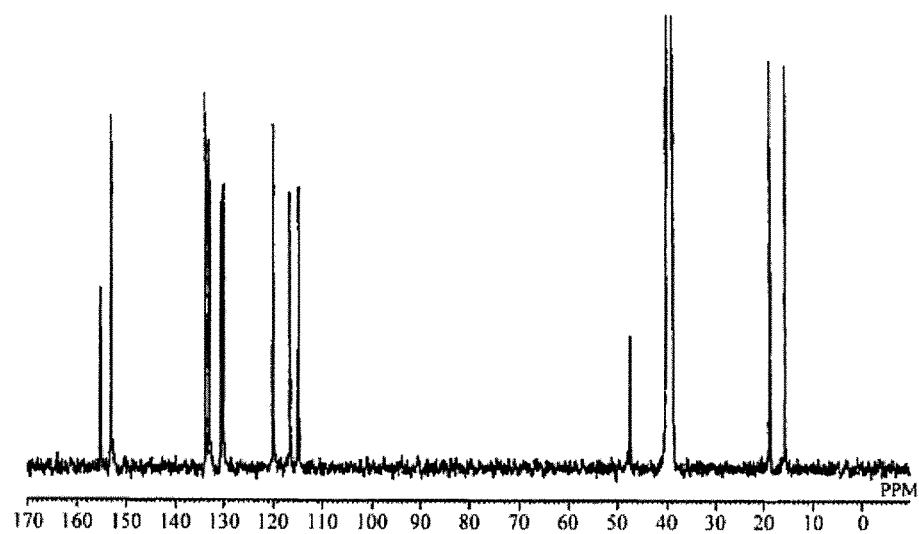
FIG. 2 is a chart of a $^{13}$C-NMR spectrum of a phenolic trinuclear compound (1) produced in Synthesis Example 1.

In a 2 L-volume four-neck flask provided with a condenser, 293.2 g (2.4 moles) of 2,5-xylenol, 122 g (1 mole) of 4-hydroxybenzaldehyde, and 500 mL of 2-ethoxyethanol were charged, and 2,5-xylenol and 4-hydroxybenzaldehye were dissolved in 2-ethoxyethanol. Then, 10 mL of sulfuric acid was added to the reaction solution in the four-neck flask under cooling in an ice bath, and then reacted under stirring by heating at 100° C. for 2 hours using a mantle heater. After the completion of reaction, water was added to the reaction solution to perform a reprecipitation operation, thereby producing a crude product. The crude product was again dissolved in acetone and reprecipitated with water. The product produced by the reprecipitation operation was filtered off, dried under vacuum to produce 213 g of a white crystal of a precursor compound (phenolic trinuclear compound (1)). As a result of GPC and $^{13}$C-NMR spectrum measurement, the phenolic trinuclear compound (1) was confirmed to be a target compound having a purity of 98.2%, by mass determined from an area ratio in GPC. FIG. 1 shows a GPC chart of the phenolic trinuclear compound (1), and FIG. 2 shows a chart of a $^{13}$C-NMR spectrum of the phenolic trinuclear compound (1).

Synthesis Example 2

Synthesis of Phenolic Trinuclear Compound

Figure 3:
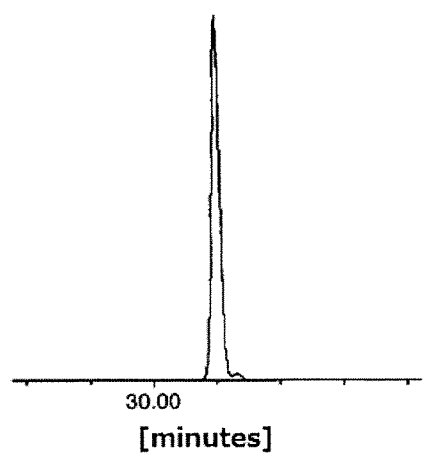
FIG. 3 is a GPC chart of a phenolic trinuclear compound (2) produced in Synthesis Example 2.
Figure 4:
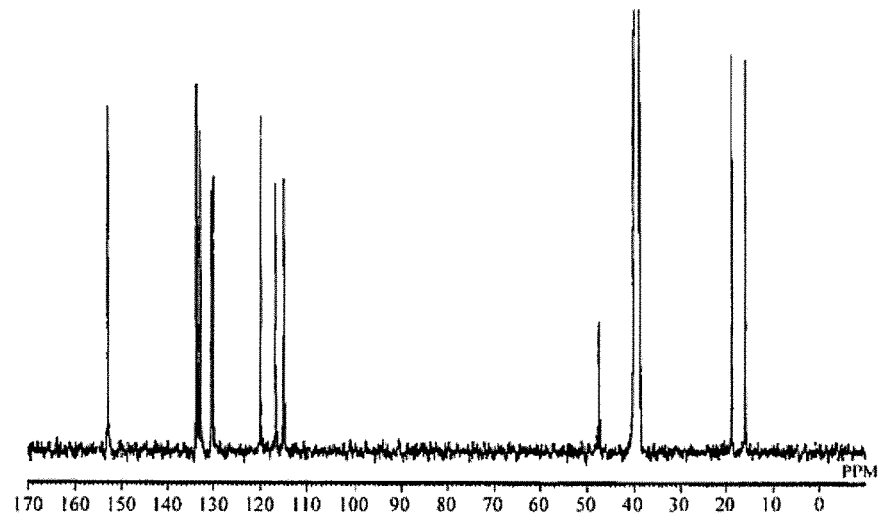
FIG. 4 is a chart a $^{13}$C-NMR spectrum of a phenolic trinuclear compound (2) produced in Synthesis Example 2.

First, 206 g of a white crystal of a precursor compound (phenolic trinuclear compound (2)) was produced by the same method as in Synthesis Example 1 except that 106.1 g (1 mole) of benzaldehyde was used in place of 122 g (1 mole) of 4-hydroxybenzaldehyde. As a result of GPC and $^{13}$C-NMR spectrum measurement, the phenolic trinuclear compound (2) was confirmed to be a target compound having a purity of 98.7% by mass determined from an area ratio in GPC. FIG. 3 shows a GPC chart of the phenolic trinuclear compound (2), and FIG. 4 shows a chart of a $^{13}$C-NMR spectrum of the phenolic trinuclear compound (2).

Synthesis Example 3

Synthesis of Novolac Phenol Resin

Figure 5:
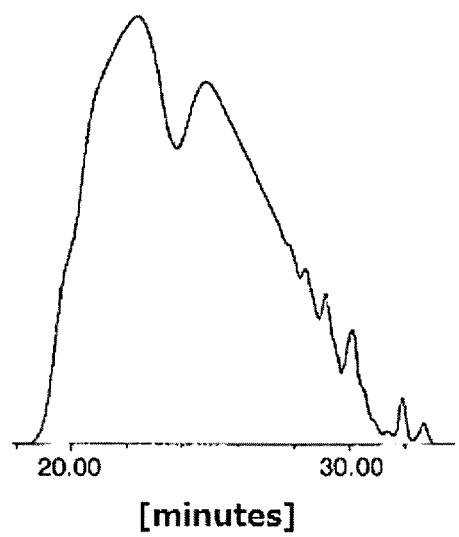
FIG. 5 is a GPC chart of a novolac resin (3-a) produced in Synthesis Example 3.

In a 300 mL-volume four-neck flask provided with a condenser, 4.2 g (0.012 moles) of the phenolic trinuclear compound (1) produced in Synthesis Example 1, 12.6 g (0.038 moles) of the phenolic trinuclear compound (2) produced in Synthesis Example 2, 1.6 g (0.05 moles) of 92% paraformaldehyde, 15 mL of 2-ethoxyethanol, and 15 mL of acetic acid were charged, and the phenolic trinuclear compound (1) and paraformaldehyde were dissolved in a mixed solvent of 2-ethoxyethanol and acetic acid (phenolic trinuclear compound (1): phenolic trinuclear compound (2)=25:75). Then, 10 mL of sulfuric acid was added to the reaction solution in the four-neck flask under cooling in an ice bath, then heated to 80° C. by using an oil bath, and reacted under stirring by heating for 4 hours. After the completion of reaction, water was added to the reaction solution to perform a reprecipitation operation, thereby producing a crude product. The resultant crude product was again dissolved in acetone and then further reprecipitated with water. The product produced by the reprecipitation operation was filtered off and dried under vacuum to produce 16.5 g of a light red powder of a novolac phenol resin (novolac resin (3-a)). FIG. 5 shows a GPC chart of the novolac resin (3-a). As a result of GPC of the novolac resin (3-a), the number-average molecular weight (Mn)=3,654, the weight-average molecular weight (Mw)=18,798, and polydispersity (Mw/Mn)=5.144.

Synthesis Example 4

Synthesis of Novolac Phenol Resin

Figure 6:
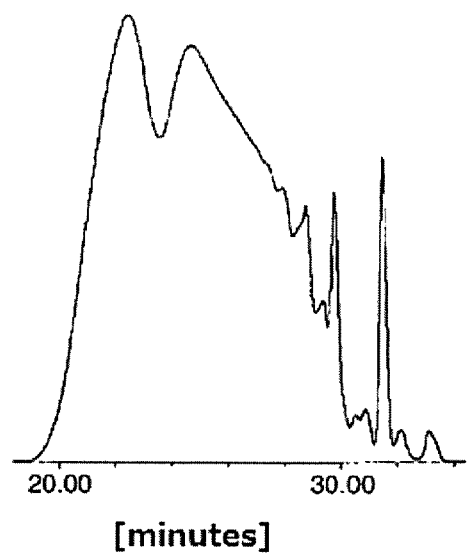
FIG. 6 is a GPC chart of a novolac resin (3-b) produced in Synthesis Example 4.

First, 16.2 g of a light red powder of a novolac phenol resin (novolac resin (3-b)) was produced by the same method as in Synthesis Example 3 except that 8.7 g (0.025 moles) of the phenolic trinuclear compound (1) produced in Synthesis Example 1 and 8.3 g (0.025 moles) of the phenolic trinuclear compound (2) produced in Synthesis Example 2 (phenolic trinuclear compound (1): phenolic trinuclear compound (2)=50:50) were used in place of 4.2 g (0.012 moles) of the phenolic trinuclear compound (1) produced in Synthesis Example 1 and 12.6 g (0.038 moles) of the phenolic trinuclear compound (2) produced in Synthesis Example 2. FIG. 6 shows a GPC chart of the novolac resin (3-b). As a result of GPC of the novolac resin (3-b), the number-average molecular weight (Mn)=2,529, the weight-average molecular weight (Mw)=11,421, and polydispersity (Mw/Mn)=4.516.

Synthesis Example 5

Synthesis of Novolac Phenol Resin

Figure 7:
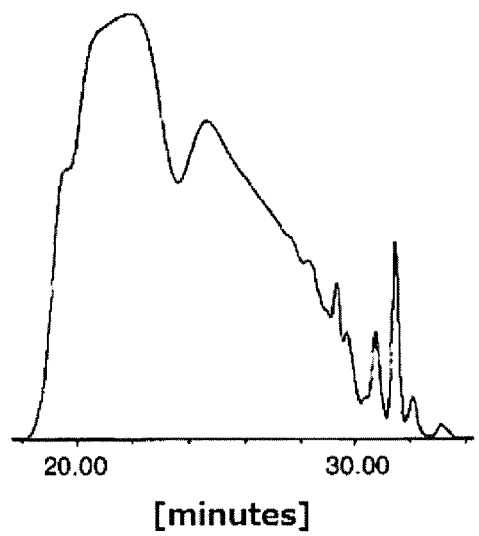
FIG. 7 is a GPC chart of a novolac resin (3-c) produced in Synthesis Example 5.

First, 16.7 g of a light red powder of a novolac phenol resin (novolac resin (3-c)) was produced by the same method as in Synthesis Example 3 except that 13.2 g (0.038 moles) of the phenolic trinuclear compound (1) produced in Synthesis Example 1 and 4.0 g (0.012 moles) of the phenolic trinuclear compound (2) produced in Synthesis Example 2 (phenolic trinuclear compound (1): phenolic trinuclear compound (2)=75:25) were used in place of 4.2 g (0.012 moles) of the phenolic trinuclear compound (1) produced in Synthesis Example 1 and 12.6 g (0.038 moles) of the phenolic trinuclear compound (2) produced in Synthesis Example 2. FIG. 7 shows a GPC chart of the novolac resin (3-c). As a result of GPC of the novolac resin (3-c), the number-average molecular weight (Mn)=3,313, the weight-average molecular weight (Mw)=25,435, and polydispersity (Mw/Mn)=7.678.

Comparative Synthesis Example 1

Synthesis of Novolac Phenol Resin

Figure 8:
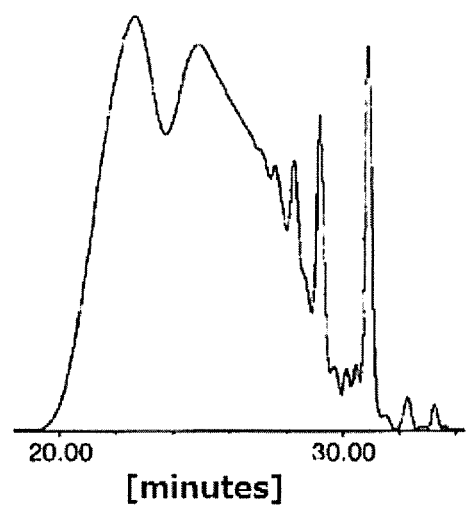
FIG. 8 is a GPC chart of a novolac resin (3-d) produced in Comparative Synthesis Example 1.

First, 16.8 g of a light red powder of a novolac phenol resin (novolac resin (3-d)) was produced by the same method as in Synthesis Example 3 except that 17.4 g (0.05 moles) of the phenolic trinuclear compound (1) produced in Synthesis Example 1 (phenolic trinuclear compound (1): phenolic trinuclear compound (2)=100:0) were used in place of 4.2 g (0.012 moles) of the phenolic trinuclear compound (1) produced in Synthesis Example 1 and 12.6 g (0.038 moles) of the phenolic trinuclear compound (2) produced in Synthesis Example 2. FIG. 8 shows a GPC chart of the novolac resin (3-d). As a result of GPC of the novolac resin (3-d), the number-average molecular weight (Mn)=2,733, the weight-average molecular weight (Mw)=10,984, and polydispersity (Mw/Mn)=4.019.

Comparative Synthesis Example 2

Synthesis of Cresol Novolac Resin

Figure 9:
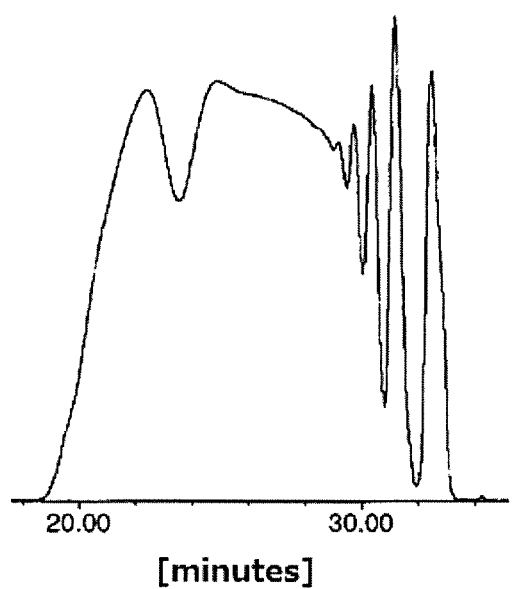
FIG. 9 is a GPC chart of a novolac resin (3-e) produced in Comparative Synthesis Example 2.

In a 2 L-volume four-neck flask provided with a thermometer and a stirrer, 648 g (6 moles) of m-cresol, 432 g (4 moles) of p-cresol, 2.5 g (0.2 moles) of oxalic acid, and 492 g of 42% formaldehyde were charged, heated to 100° C., and reacted. After the completion of reaction, the reaction solution was dehydrated and distilled up to 200° C. under normal pressure and then distilled under reduced pressure at 230° C. for 6 hours to produce 736 g of a yellow solid of novolac resin (novolac resin (3-e)). FIG. 9 shows a GPC chart of the novolac resin (3-e). As a result of GPC of the novolac resin (3-e), the number-average molecular weight (Mn)=1,450, the weight-average molecular weight (Mw)=10,316, and polydispersity (Mw/Mn)=7.116.

Examples 1 to 3 and Comparative Examples 1 and 2

For the novolac resins (3-a) to (3-e) synthesized in Synthesis Examples 3 to 5 and Comparative Synthesis Examples 1 and 2, each of the novolac resins, a photosensitizer "P-200" (condensate of 4,4'-[1-[4-[1-(4-hydroxyphenyl)-1-methylethyl]phenyl]ethylidene]bisphenol (1 mole) and 1,2-naphthoquinone-2-diazide-5-sulfonyl chloride (2 moles)) (manufactured by Toyo Gosei Co., Ltd.), and propylene glycol monomethyl ether acetate (PGMEA) were mixed at 20/5/75 (mass ratio), dissolved, and then filtered by using a 0.2 μm membrane filter to prepare a photosensitive composition.

For measuring sensitivity, a composition (novolac resin/PGMEA=20/80 (mass ratio)) was prepared as a photosensitive composition without a photosensitizer by dissolving the novolac resin in PGMEA.

<Measurement of Alkali Developability>

The photosensitive composition was applied on a 5-inch silicon wafer by using a spin coater and dried for 60 seconds on a hot plate of 110° C. to form a thin film having a thickness of about 1 μm. The wafer was immersed in a developer (2.38% aqueous tetramethylammonium hydroxide solution) for 60 seconds and then dried on a hot plate of 110° C. for 60 seconds. The thickness of a coating film of the photosensitive composition was measured before and after immersion in the developer, and a value obtained by dividing a difference in thickness by 60 was considered as an alkali dissolution rate (ADR (nm/sec)) and used for evaluating the alkali developability. The thickness of the coating film was measured by using a thickness meter ("F-20" manufactured by Filmetrics Inc.).

<Evaluation of Sensitivity>

The photosensitive composition was applied to a thickness of about 1 μm and dried on a wafer, and a mask corresponding to a resist pattern of 1 to 10 μm having a line-and-space of 1:1 was adhered to the wafer. Then, an exposure amount (Eop exposure amount) which permitted faithful reproduction with L/S=3 μm using a g/h/i line lamp (multi-light manufactured by Ushio Inc.) was determined.

Evaluation of Resolution

A photomask was placed on a silicon wafer on which the photosensitive composition had been applied and dried, and exposed to light by irradiation with a g-h-i line lamp (multi-light manufactured by Ushio Inc.) with 200 mJ/cm$^2$. After irradiation, the coating film was developed and dried by the same method as in ADR measurement. The pattern state of a resist pattern on the wafer after development was evaluated by using a laser microscope (VK-X200) manufactured by Keyence Corporation. In evaluation, when resolution with L/S=5 μm was possible, resolution was evaluated as "A", while when resolution with L/S=5 μm was impossible, resolution was evaluated as "B".

Evaluation of Heat Resistance

A PGMEA solution with a solid content of 40% by mass was prepared as a photosensitive composition by dissolving the novolac resin in PGMEA and used for evaluating heat resistance. The photosensitive composition was applied to a thickness of about 1 μm on a 5-inch silicon wafer by using a spin coater and then dried on a hot plate of 110° C. for 60 seconds. The resin part was scraped off from the resultant wafer, and Tg was measured. Tg was measured by scanning with a differential scanning calorimeter "(DSC) Q100" (manufactured by TA Instruments Inc.) in a nitrogen atmosphere under the conditions of a temperature range of −100° C. to 200° C. and a heating rate of 10° C./min. The measured result was regarded as a glass transition temperature (Tg).

Measurement of Absorbance

The novolac resin was dissolved in PGMEA to prepare a PGMEA solution with a solid content of 1% by mass. The absorbance of the prepared PGMEA solution was measured at each of the wavelengths of 365 nm, 405 nm, and 436 nm corresponding to the visible region. The absorbance was measured by using a quartz-made measurement cell (optical path length: 10 mm, optical path width: 10 mm) installed in an ultraviolet-visible spectrophotometer "UV-1600" (manufactured by Shimadzu Corporation). The set parameters included a spectral band width of 2 nm, a measurement wavelength range of 190 to 750 nm, a wavelength scale of 25 nm/cm, and a scan speed of 100 nm/min.

TABLE 1

| | Example 1 | Example 2 | Example 3 | Comparative Example 1 | Comparative Example 2 |
|---|---|---|---|---|---|
| Novolac resin used | (3-a) | (3-b) | (3-c) | (3-d) | (3-e) |
| | | Evaluation | | | |
| ADR (nm/sec) | 60 | 120 | 150 | 220 | 11 |
| Sensitivity (mJ) | 50 | 70 | 85 | 95 | 200 |
| Resolution | A | A | A | A | A |
| Heat resistance (Tg) (° C.) | >200 | >200 | >200 | >200 | 110 |
| Absorbance 365 nm | 0.165 | 0.204 | 0.286 | 0.330 | 0.156 |
| 405 nm | 0.102 | 0.109 | 0.153 | 0.185 | 0.058 |
| 436 nm | 0.053 | 0.093 | 0.148 | 0.175 | 0.033 |

As a result, the photosensitive compositions (Examples 1 to 3 and Comparative Example 1) containing the novolac resins (3-a) to (3-d), respectively, which were novolac phenol resins, had good sensitivity and heat resistance as compared with the novolac resin (3-e) which was the cresol novolac resin. Also, comparison between the novolac resins (3-a) to (3-d) shows the tendency that ADR is increased and sensitivity is improved as the content ratio of the phenolic trinuclear compound (1) produced in Synthesis Example 1 increases. There was also the tendency that the absorbance at 365 to 436 nm decreases as the content ratio of the phenolic trinuclear compound (2) produced in Synthesis Example 2 increases.

The invention claimed is:

1. A novolac phenol resin comprising a product of a reaction under an acid catalyst using, as essential reaction raw materials, a phenolic trinuclear compound (A1), one or more phenolic trinuclear compounds (A2), and an aldehyde (B), the phenolic trinuclear compound (A1) being represented by general formula (1) below,

[Chem. 1]

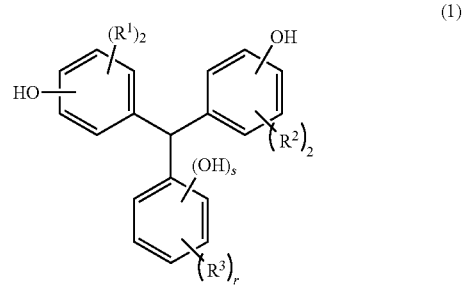

(1)

in the formula (1), $R^1$, $R^2$, and $R^3$ each independently represent an alkyl group having 1 to 8 carbon atoms, which may have a substituent, the plurality of $R^1$ present may be the same or different, the plurality of $R^2$ present may be the same or different, when a plurality of $R^3$ are present, they may be the same or different, r represents an integer of 0 to 4, s represents 1 or 2, and the sum of r and s is 5 or less, and the phenolic trinuclear compounds (A2) being selected from the group consisting of compounds represented by general formulae (2-1), (2-2), (2-3) and (2-4) below,

[Chem. 2]

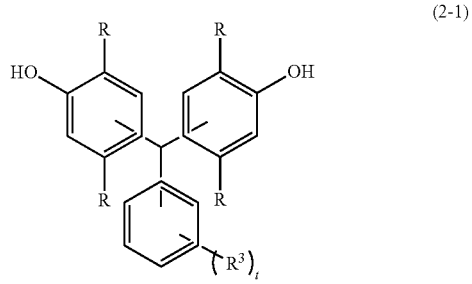

(2-1)

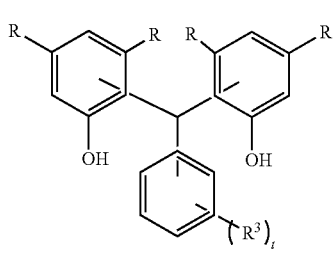

(2-2)

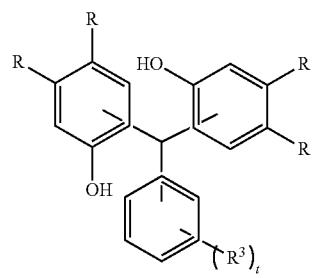

(2-3)

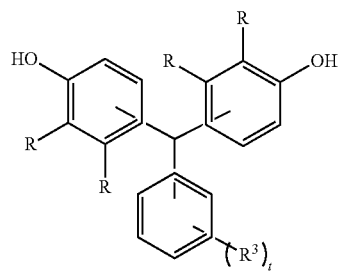

(2-4)

in the formulae, R represents an alkyl group having 1 to 8 carbon atoms, which may have a substituent, the plurality of R present may be the same or different, $R^3$ represents an alkyl group having 1 to 8 carbon atoms, which may have a substituent, when a plurality of $R^3$ are present, they may be the same or different, and t represents an integer of 0 to 5, wherein the molar ratio of the phenolic trinuclear compound (A1) to the phenolic trinuclear compound (A2) is 20:80 to 90:10.

2. The novolac phenol resin according to claim 1, wherein the novolac phenol resin has, as a repeating unit, one or more structural parts selected from the group consisting of a structural part (II-1) represented by general formula (I-1) below,

[Chem. 3]

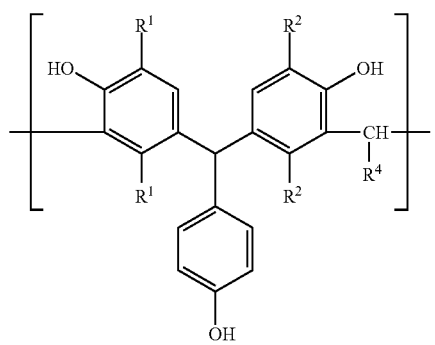

(I-1)

in the formula (I-1), $R^1$ and $R^2$ each independently represent an alkyl group having 1 to 8 carbon atoms, which may have a substituent, the plurality of $R^1$ present may be the same or different, the plurality of $R^2$ present may be the same or different, and $R^4$ represents a hydrogen atom, an alkyl group which may have a substituent, or an aryl group which may have a substituent, and a structural part (I-1) represented by general formula (II-1) below,

[Chem. 4]

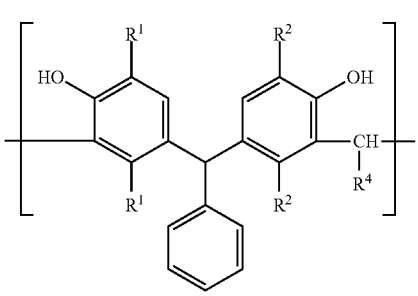

(II-1)

in the formula (II-1), $R^1$, $R^2$, and $R^4$ represent the same meanings as in the formula (I-1).

3. The novolac phenol resin according to claim 1, wherein the weight-average molecular weight is 5,000 to 35,000.

4. A photosensitive composition comprising the novolac phenol resin according to claim 1.

5. A resist material comprising the photosensitive composition according to claim 4.

6. A novolac phenol resin composition comprising:
a novolac phenol resin (A1) which is a product of a reaction of a phenolic trinuclear compound (A1) with an aldehyde (B), the phenolic trinuclear compound (A1) being the phenolic trinuclear compound (A1) being represented by general formula (1) below,

[Chem. 5]

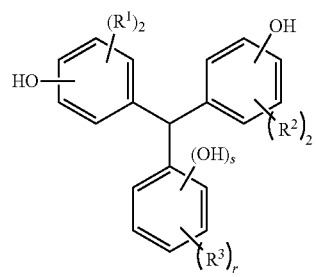

(1)

in the formula (1), $R^1$, $R^2$, and $R^3$ each independently represent an alkyl group having 1 to 8 carbon atoms, which may have a substituent, the plurality of $R^1$ present may be the same or different, the plurality of $R^2$ present may be the same or different, when a plurality of $R^3$ are present, they may be the same or different, r represents an integer of 0 to 4, s represents 1 or 2, and the sum of r and s is 5 or less; and a novolac phenol resin (A2) which is a product of a reaction of one or more phenolic trinuclear compounds (A2) with an aldehyde (B), the phenolic trinuclear compounds (A2) being selected from the group consisting of compounds represented by general formulae (2-1), (2-2), (2-3) and (2-4) below,

[Chem. 6]

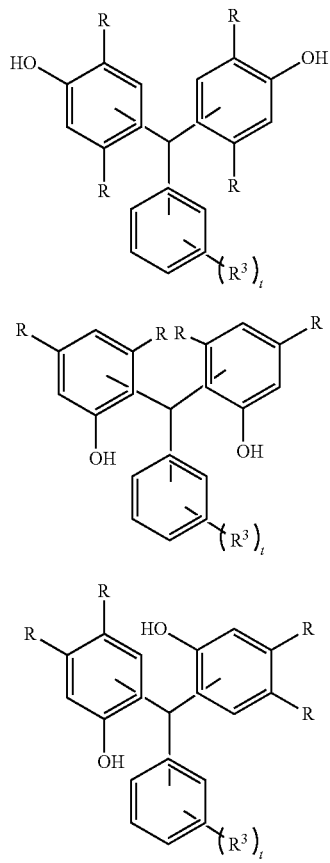

(2-1)

(2-2)

(2-3)

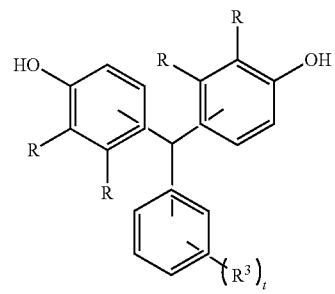

(2-4)

in the formulae, R represents an alkyl group having 1 to 8 carbon atoms, which may have a substituent, the plurality of R present may be the same or different, $R^3$ represents an alkyl group having 1 to 8 carbon atoms, which may have a substituent, when a plurality of $R^3$ are present, they may be the same or different, and t represents an integer of 0 to 5.

7. The novolac phenol resin composition according to claim 6, wherein the content ratio of the novolac phenol resin (A1) to the novolac phenol resin (A2) is such that the molar ratio of a structural unit derived from the phenolic trinuclear compound (A1) to a structural unit derived from the phenolic trinuclear compound (A2) is within a range of 20:80 to 90:10.

8. A photosensitive composition comprising the novolac phenol resin composition according to claim 6 and a photosensitizer.

9. A resist material comprising the photosensitive composition according to claim 8.

* * * * *